US008974800B2

(12) United States Patent
Gennaro

(10) Patent No.: US 8,974,800 B2
(45) Date of Patent: Mar. 10, 2015

(54) PROTEINS EXPRESSED BY MYCOBACTERIUM TUBERCULOSIS AND NOT BY BCG AND THEIR USE AS DIAGNOSTIC REAGENTS AND VACCINES

(71) Applicant: University of Medicine & Dentistry of New Jersey, Somerset, NJ (US)

(72) Inventor: Maria Laura Gennaro, New York, NY (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 0 days.

(21) Appl. No.: 13/893,659

(22) Filed: May 14, 2013

(65) Prior Publication Data

US 2013/0251739 A1    Sep. 26, 2013

Related U.S. Application Data

(60) Division of application No. 13/198,108, filed on Aug. 4, 2011, which is a continuation of application No. 12/503,717, filed on Jul. 15, 2009, now Pat. No. 8,021,832, which is a continuation of application No. 11/677,502, filed on Feb. 21, 2007, now Pat. No. 7,579,141, which is a division of application No. 10/009,383, filed as application No. PCT/US00/12257 on May 4, 2000, now Pat. No. 7,932,373.

(60) Provisional application No. 60/132,505, filed on May 4, 1999.

(51) Int. Cl.
| | |
|---|---|
| A61K 39/04 | (2006.01) |
| A61K 39/02 | (2006.01) |
| A61K 39/00 | (2006.01) |
| C07K 14/35 | (2006.01) |
| G01N 33/569 | (2006.01) |
| G01N 33/50 | (2006.01) |
| A61K 38/00 | (2006.01) |

(52) U.S. Cl.
CPC .............. *A61K 39/04* (2013.01); *A61K 38/00* (2013.01); *A61K 39/00* (2013.01); *A61K 2039/53* (2013.01); *C07K 14/35* (2013.01); *G01N 33/5695* (2013.01); *G01N 33/5091* (2013.01); *Y10S 435/863* (2013.01)
USPC .................. 424/248.1; 424/184.1; 424/185.1; 424/234.1; 435/863

(58) Field of Classification Search
USPC ...................... 424/184.1, 185.1, 234.1, 248.1; 530/300, 350
See application file for complete search history.

(56) References Cited

U.S. PATENT DOCUMENTS

| | | | |
|---|---|---|---|
| 6,291,190 | B1 | 9/2001 | Behr et al. |
| 6,436,409 | B1 | 8/2002 | Gicquel et al. |
| 7,579,141 | B2 | 8/2009 | Gennaro |
| 7,709,211 | B2 | 5/2010 | Gennaro |
| 7,932,373 | B1 | 4/2011 | Gennaro |
| 8,021,832 | B2 | 9/2011 | Gennaro |
| 2007/0224122 | A1 | 9/2007 | Gennaro |
| 2007/0224123 | A1 | 9/2007 | Gennaro |
| 2010/0016415 | A1 | 1/2010 | Gennaro |
| 2011/0052637 | A1 | 3/2011 | Gennaro |

FOREIGN PATENT DOCUMENTS

| | | |
|---|---|---|
| WO | 97/09428 A2 | 3/1997 |
| WO | 9709429 A2 | 3/1997 |
| WO | 98/16645 A2 | 4/1998 |
| WO | 98/16646 A2 | 4/1998 |
| WO | 98/44119 A1 | 10/1998 |
| WO | 99/04005 A1 | 1/1999 |
| WO | 0011214 A1 | 3/2000 |
| WO | 00/66157 A1 | 11/2000 |
| WO | 0179274 A2 | 10/2001 |
| WO | 03/093307 A2 | 11/2003 |

OTHER PUBLICATIONS

French, S. et al. What is a conservative substitution? Journal of Molecular Evolution, vol. 19, pp. 171-175, 1983.*
Wagstaff and Zellweger, Mol. Diag. Ther, (2006) 10(1). 57-63.
Fishi et al., Microbiology (1996) 142, 3147-3161.
Tissot et al., CID (2005) 40, 211-217.
Colangeli et al. (2000) Infection and Immunity 68(2):990-993.
Berthet et al., (1998), "*mycobacterium* tuberculosis operon encoding ESAT-6 and a novel low-molecular-mass culture filtrate protein (CFP-10)", Microbiol., 144:3195-3203.
Andersen et al., "Structure and Mapping of Antigenic Domains of Protein Antigen b, a 38,000-Molecular-Weight Protein of *Mycobacterium* tuberculosis," Infect Immun. vol. 57(8), pp. 2481-2488 (Aug. 1989).
Butler, John E., "Enzyme-Linked Immunosorbent Assay", Immunochemistry, 1994, pp. 759-803.
Cockle, P.J., et al., "Indentification of Novel *Mycobacterium* tuberculosis Antigens with Potential as Diagnostic Reagents or Subunit Vaccine Candidates by Comparative Genomics", Infection and immunity, vol. 70, No. 12, Dec. 2002, pp. 6996-7003.
Di Fabio, Simonetta, et al., "Quantitation of Human Influenza Virus-Specific Cytotoxic T Lymphocytes: Correlation of Cytotoxicity and Increased Numbers of IFN-Gamma Producing CD8+ T Cells", International Immunology, vol. 6, No. 1, pp. 11-19.
Lalvani, Ajit, et al., "Rapid Effector Function in CD8+ T Cells", Journal of Experimental Medicine, vol. 186. No. 6, Sep. 15, 1997, pp. 859-865.
Lalvani, Ajit, et al., "Human Cytolytic and Interferon Gamma-Secreting CD8+ T Lymphocytes Specific for *Mycobacterium* tuberculosis", Proceedings of the National Academy of Sciences of the United States of America, vol. 95, Jan. 1998, pp. 270-275.

(Continued)

*Primary Examiner* — Rodney P Swartz
(74) *Attorney, Agent, or Firm* — Fox Rothschild LLP; Gerard P. Norton; Jianming Jimmy Hao

(57) ABSTRACT

The present invention is directed to reagents useful for generating immune responses to *Mycobacterium tuberculosis* and for diagnosing infection and disease in a subject that has been exposed to *M. tuberculosis*.

7 Claims, 8 Drawing Sheets

(56) References Cited

OTHER PUBLICATIONS

Lalvani, Ajit, et al., "Potent Induction of Focused Th1-Type Cellular and Humoral Immune Responses by RTS, S/SBAS2, a Recombinant Plasmodium falciparum Malaria Vaccine", The Journal of Infection Diseases, vol. 180, 1999, pp. 1656-1664.
Lalvani, Ajit, et al., "Rapid Detection of *Mycobacterium* tuberculosis Infection by Enumeration of Antigen-specific T Cells", American Journal of Respiratory and Critical Care Medicine, vol. 163, 2001, pp. 824-828.
Liu, Xiao-Qing, et al., "Evaluation of T-Cell Responses to Novel RD1- and RD2-Encoded *Mycobacterium* tuberculosis Gene Products for Specific Detection of Human Tuberculosis Infection", Infection and Immunity, May 2004, pp. 2574-2581.
Sedgwick, Jonathon, et al., "Detection of Cell-Surface Molecules, Secreted Products of Single Cells and Cellular Proliferation by Enzyme Immunoassay", Journal of Immunological Methods, vol. 150, 1992, pp. 159-175.
Ait-Khaled, Nadia, et al. "Tuberculosis: A manual for Medical Students", Chapter 1, World Health Organization 2003. pp. 1-34.
Letter to European Patent Office in Reference to Third Party Observations Under Article 115 EPC. Feb. 13, 2009.
Berthet et al., (1998), "A *Mycobacterium* tuberculosis operon encoding ESAT-6 and a novel low-molecular-mass culture filtrate protein(CFP-10)", Microbiol., 144:3195-3203.
Cole et al., "*Mycobacterium* tuberculosis H37Rv complete genome: segment 160/162", Database EBI, Accession No. AL022120 XP002218539, referring to Cole et al., (1998) "Deciphering the bilogy of *Mycobacterium* tuberculosis from the complete genomesequence", Nature, 393:537-544.
Mahairas et al., 1996, "Molecular Analysis of Genetic Differences between *Mycobacterium bovis* BCG and Virulent *M. bovis*", J. Bacteriol., 178(5):1274-1282.
EP Search Report dated Dec. 23, 2002.
EP Search Report dated Apr. 28, 2003.
Colangeli et al (200) Infection and Immunity 68(2):990-993.
Lyaschencko et al. (1998) Infection and Immunity 66(8):3606-3610.
Manca et al. (1997) Infection and Immunity 65(1):16-23.
Manca et al. (1997) Infection and Immunity 65(12):4951-4957.
Ait-Kahaled et al., Tuberculosis: A Manual for medical students, Chapter 1—The basic science of tuberculosis (2003).
Harboe et al., "Evidence for occurrence of the ESAT-6 protein in *Mycobacterium* tuberculsis virulent *Mycobacterium bovis* and for its absence in *Mycobacterium bovis* BCG," Infection and Immunity, 64:16-22 (Jan. 1996).
Opposition of GlaxoSmithKline Biologicals SA filed against European Patent No. EP1214008, Nov. 30, 2009.
Opposition of Statens Serum Institut filed against European Patent No. EP1214088, Jan. 21, 2010.
Ait-Khaled, Nadia, et al., "Tuberculosis: A Manual for Medical Students", Chapter 1, World Health Organization 2003, p. 1-34.
Letter to European Patent Office in Reference to Third Party Observations Under Article 115 EPC, Feb. 13, 2009.
Buddle, Bryce M., et al., Differentiation Between *Mycobacterium bovis* BCG-Vaccinated and *M. bovis*-Infected Cattle by Using Recombinant Mycobacterial Antigens, Clin. Diag. Lab. Immunol., vol. 6, No. 1, pp. 1-5, 1999.
Butler, John E., "Enzyme-Linked Immunosorbent Assay", Immunochemistry, 1994, p. 759-803.
Cockle, P.J., et al., "Indentification of Novel *Mycobacterium tuberculosis* Antigens with Potential as Diagnostic Reagents or Subunit Vaccine Candidates by Comparative Genomis", Infection and Immunity, vol. 70, No. 12, Dec. 2002, p. 6996-7003.
DiFabio, Simonetta, et al., "Quanitation of Human Influenza Virus-Specific Cytotoxic T Lymphocytes: Correlation of Cytotoxicity and Increased Numbers of IFN-Gamma Producing CD8+ T Cells", International Immunology, vol. 6, No. 1, p. 11-19.
Lalvani, Ajit, et al., "Rapid Effector Fuction in CD8+ Memory T Cells", Journal of Experimental Medicine, vol. 186, No. 6, Sep. 15, 1997, p. 859-865.
Lalvani, Ajit, et al., "Human Cytolytic and Interferon Gamma-Secreting CD8+ T Lymphocytes Specific for *Mycobacterium* tuberculosis", Proceedings of the National Academy of Sciences of the United States of America, vol. 95, Jan. 1998, p. 270-275.
Lalvani, Ajit, et al., Potent Induction of Focused Th1-Type Cellular and Humoral Immune Responses by RTS, S/SBAS2, a Recombinant *Plasmodium falciparum* Malaria Vaccine. The journal of Infection Diseases, vol. 180, 1999, p. 1656-1664.
Lalvani, Ajit, et al., "Rapid Detection of Mycobacterium tuberculosis Infection by Enumeration of Antigen-specific T Cells", American Journal of Respiratory and critical Care Medicine, vol. 163, 2001, p. 824-828.
Liu, Xia-Qing, et al., "Evaluation of T-Cell responses to Novel RD1- and RD2-Encoded *Mycobacterium* tuberculosis Gene Products for Specific Detection of Human Tuberculosos Infection", Infection and Immunity, May 2004, p. 2574-2581.
Sedgwick, Jonathon, et al., "Detection of Cell-Surface Molecules. Secreted Products of Single Cells and Cellular Proliferation by Enzyme Immunoassay", Journal of Immunological Methods, vol. 150, 1992, p. 159-175.
Andersen, se Bengard, et al., "Structure and Mapping of Antigenic Domains of Protein Antigen b, a 38,000-Molecular-Weight protein of *Mycobacterium* tuberculosis", Infect Immun., vol. 57(8), p. 3481-2488 (Aug. 1989).
Colangeli, R., et al., "MTSA-10 the Product of the RV3874 Gene of *Mycobacterium* tuberculosis, Elicits Tuberculosis-Specific, Delayed-Type Hypersensitivity in Guinea Pigs", Infect Immun., vol. 68(2), p. 990-993 (Feb. 2000).
Lyashchenko, K., et al., "Use of *Mycobacterium* tuberculosis Complex-Specific Antigen Coacktails for a Skin Test for Tuberculosis", Infect Immun., vol. 66(8), p. 3606-3610 (Aug. 1998).
Manca, C., et al., "Molecular Cloning, Purification, and Serological Characterization of MPT63, a Novel Antigen Seceted by *Mycobacterium* tuberculosis", Infect Immun., vol. 65(1), p. 16-23 (Jan. 1997).
Manca, C., et al., "MTC28, a novel 28-Kilodalton Proline-Rich Secreted Antigen specific for the Mycobacterium tuberculosis Complex", Infect Immun., vol. 65(12), p. 4951-4957 (Dec. 1997).
Berthet et al., "A *Mycobacterium* tuberculosis Operon Encoding ESAT-6 and a Novel Low-Molecular-Mass Culture Filtrate Protein (CFP-10)", Microbiol., vol. 144, p. 3195-3203.
Cole, et al., "*Mycobacterium* tuberculosis H37Rv Complete Genome; Segment 160/162", Database EBI, Accession No. AL022120 XP002218539, referring to: Cole, et al., "Deciphering the Biology of *Mycobacterium* tuberculosis from the Complete GenomeSequence", Nature, vol. 393, p. 537-544 (Jun. 1998).
Mahairas, et al., "Molecular Analysis of Genetic Differences Between *Mycobacterium bovis* BCG and Virulent *M. bovis*", J. Bacteriol., vol. 178, No. 5, p. 1274-1282 (Mar. 1996).
Cole, S.T., et al., "Deciphering the Biology of Mycobbacterium tuberculosis from the Complete Genome Sequence," Nature, vol. 396, Nov. 12, 1998.
Abbas, Abul K. et al. Text and Review Series, Cellular and Molecular Immunology, 3rd ed. Philadephia, PA: W.B. Saunders Co., 1997, Chapter 13, pp. 280-288.
Ravn et al. (Mar. 1999), Journal of Infectious Diseases, vol. 179, pp. 637-645.
Ulrichs et al. (1998), European Journal of Immunology, vol. 28, pp. 3949-3958.
Vordermeier et al. (1991), Journal of Immunology, vol. 147, pp. 1023-1029.
Haslov, K. et al. (1990), Scand. J. Immunol., vol. 31, pp. 503-514.
Shams et al. (2004), Journal of Immunology. vol. 173, pp. 1966-1977.
Engelhard (1994), Annual Reviews of Immunology, vol. 12, pp. 181-207.
Germain (1995), Annals of the New York Academy of Sciences, vol. 754, pp. 114-125.
Elhay, Martin J. et al., (1998), Infection and Immunity, vol. 66(7), pp. 3454-3456.
Haga, Shinji et al. (1995) J. of Leucocyte Biology, vol. 57, pp. 221-225.
Roche et al. (1996). Scandinavian Journal of Immunology, vol. 43, pp. 662-670.

(56) References Cited

OTHER PUBLICATIONS

Harboe et al., "Evidence for occurrence of the ESAT-6 protein in *Mycobacterium* tuberculosis and virulent *Mycobacterium bovis* and for its absence in *Mycobacterium bovis* BCG," Infection and Immunity, 64:16-22 (Jan. 1996).
Opposition of GlaxoSmithKline Biologicals SA filed against European Patent No. EP1214088, Nov. 30, 2009.
Response by University of Medicine and Dentistry of New Jersey to Opposition of European Patent No. EP1214088, Sep. 10, 2010.
Lavani et al., Journal of Infectious Diseases (2001) 183, 469-477.
Interlocutory Decision in opposition Proceedings (Art. 101(3)(a) and 106(2) EPC) issued on European Patent Application No. 00928851.5, Nov. 13, 2012.
Kinman (1994) current protocols in Immunology 6(19):196; 19-8.
Poulter (1983) clinical & Exprimental Immunology 53:513-520.
Velaz-Faircloth et al., (1999) Infectino and Immunity 67(8):4243-4250.
GlaxoSmith Kline Response filed Aug. 12, 2013 in Opposition of EP1214088.
Declaration of François-Xavier Berthet submitted with GlaxoSmith Kline response filed Aug. 12, 2013 in Opposition of EP 1214088.
Declaration of Anja Olsen submitted with GlaxoSmith Kline response filed Aug. 12, 2013 in Opposition of EP 1214088.
Pathan et al., High Frequencies of IFN-g—Secreting CD4+ Cells Recognising Multiple Epitopes in Esat-6 in Tuberculosis Patients and Healthy Contacts, Abstract, submitted with GlaxoSmith Kline response filed Aug. 12, 2013 in Opposition of EP 1214088.
E-mail date May 28, 1998 from jrothel@csl.com.au, submitted with GlaxoSmith Kline response filed Aug. 12, 2013 in Opposition of EP 1214088.
François-Xavier et al., Contribution to the study of proteins exported by M. tuberculosis, Extract.

* cited by examiner

MTBN1
MTAEPEVRTLREVVLDQLGTAESRAYKMWLPPLTNPVPLNELIARDRRQPLRFALGIMDE
PRRHLQDVWGVDVSGAGGNIGIGGAPQTGKSTLLQTMVMSAAATHSPRNVQFYCIDLGGG
GLIYLENLPHVGGVANRSEPDKVNRVVAEMQAVMRQRETTFKEHRVGSIGMYRQLRDDPS
QPVASDPYGDVFLIIDGWPGFVGEFPDLEGQVQDLAAQGLAFGVHVIISTPRWTELKSRV
RDYLGTKIEFRLGDVNETQIDRITREIPANRPGRAVSMEKHHLMIGVPRFDGVHSADNLV
EAITAGVTQIASQHTEQAPPVRVLPERIHLELDPNPPGPESDYRTRWEIPIGLRETDLT
PAHCHMETNPHLLIFGAAKSGKTTIAHAIARAICARNSPQQVRFMLADYRSGLLDAVPDT
HLLGAGAINRNSASLDEAVQALAVNLKKRLPPTDLTTAQLRSRSWWSGPDVVLLVDDWHM
IVGAAGGMPPMAPLAPLLPAAADIGLHIIVTCQMSQAYKATMDKFVGAAFGSGAPTMFLS
GEKQEFPSSEFKVKRRPPGQAFLVSPDGKEVIQAPYIEPPEEVFAAPPSAG

MTBN2
MEKMSHDPIAADIGTQVSDNALHGVTAGSTALTSVTGLVPAGADEVSAQAATAFTSEGIQ
LLASNASAQDQLHRAGEAVQDVARTYSQIDDGAAGVFAE

MTBN3
MLWHAMPPELNTARLMAGAGPAPMLAAAAGWQTLSAALDAQAVELTARLNSLGEAWTGGG
SDKALAAATPMVVWLQTASTQAKTRAMQATAQAAAYTQAMATTPSLPEIAANHITQAVLT
ATNFFGINTIPIALTEMDYFIRMWNQAALAMEVYQAETAVNTLFEKLEPMASILDPGASQ
STTNPIFGMPSPGSSTPVGQLPPAATQTLGQLGEMSGPMQQLTQPLQQVTSLFSQVGGTG
GGNPADEEAAQMGLLGTSPLSNHPLAGGSGPSAGAGLLRAESLPGAGGSLTRTPLMSQLI
EKPVAPSVMPAAAAGSSATGGAAPVGAGAMGQGAQSGGSTRPGLVAPAPLAQEREEDDED
DWDEEDDW

MTBN4
MAEMKTDAATLAQEAGNFERISGDLKTQIDQVESTAGSLQGQWRGAAGTAAQAAVVRFQE
AANKQKQELDEISTNIRQAGVQYSRADEEQQQALSSQMGF

MTBN5
MAADYDKLFRPHEGMEAPDDMAAQPFFDPSASFPPAPASANLPKPNGQTPPPTSDDLSER
FVSAPPPPPPPPPPPPPTPMPIAAGEPPSPEPAASKPPTPPMPIAGPEPAPPKPPTPPMP
IAGPEPAPPKPPTPPMPIAGPAPTPTESQLAPPRPPTPQTPTGAPQQPESPAPHVPSHGP
HQPRRTAPAPPWAKMPIGEPPPAPSRPSASPAEPPTRPAPQHSRRARRGHRYRTDTERNV
GKVATGPSIQARLAEEASGAQLAPGTEPSPAPLGQPRSYLAPPTRPAPTEPPPSPSPQR
NSGRRAERRVHPDLAAQHAAAQPDSITAATTGGRRRKRAAPDLDATQKSLRPAAKGPKVK
KVKPQKPKATKPPKVVSQRGWRHWVHALTRINLGLSPDEKYELDLHARVRRNPRGSYQIA
VVGLKGGAGKTTLTAALGSTLAQVRADRILALDADPGAGNLADRVGRQSGATIADVLAEK
ELSHYNDIRAHTSVNAVNLEVLPAPEYSSAQRALSDADWHFIADPASRFYNLVLADCGAG
FFDPLTRGVLSTVSGVVVVASVSIDGAQQASVALDWLRNNGYQDLASRACVVINHIMPGE
PNVAVKDLVRHFEQQVQPGRVVVMPWDRHIAAGTEISLDLLDPIYKRKVLELAAALSDDF
ERAGRR

FIG 1A

MTBN6
LSAPAVAAGPTAAGATAARPATTRVTILTGRRMTDLVLPAAVPMETYIDDTVAVLSEVLE
DTPADVLGGFDFTAQGVWAFARPGSPPLKLDQSLDDAGVVDGSLLTLVSVSRTERYRPLV
EDVIDAIAVLDESPEFDRTALNRFVGAAIPLLTAPVIGMAMRAWWETGRSLWWPLAIGIL
GIAVLVGSFVANRFYQSGHLAECLLVTTYLLIATAAALAVPLPRGVNSLGAPQVAGAATA
VLFLTLMTRGGPRKRHELASFAVITAIAVIAAAAAFGYGYQDWVPAGGIAFGLFIVTNAA
KLTVAVARIALPPIPVPGETVDNEELLDPVATPEATSEETPTWQAIIASVPASAVRLTER
SKLAKQLLIGYVTSGTLILAAGAIAVVVRGHFFVHSLVVAGLITTVCGFRSRLYAERWCA
WALLAATVAIPTGLTAKLIIWYPHYAWLLLSVYLTVALVALVVVGSMAHVRRVSPVVKRT
LELIDGAMIAAIIPMLLWITGVYDTVRNIRF

MTBN7
MAEPLAVDPTGLSAAAAKLAGLVFPQPPAPIAVSGTDSVVAAINETMPSIESLVSDGLPG
VKAALTRTASNMNAAADVYAKTDQSLGTSLSQYAFGSSGEGLAGVASVGGQPSQATQLLS
TPVSQVTTQLGETAAELAPRVVATVPQLVQLAPHAVQMSQNASPIAQTISQTAQQAAQSA
QGGSGPMPAQLASAEKPATEQAEPVHEVTNDDQGDQGDVQPAEVVAAARDEGAGASPGQQ
PGGGVPAQAMDTGAGARPAASPLAAPVDPSTPAPSTTTTL

MTBN8
MSITRPTGSYARQMLDPGGWVEADEDTFYDRAQEYSQVLQRVTDVLDTCRQQKGHVFEGG
LWSGGAANAANGALGANINQLMTLQDYLATVITWHRHIAGLIEQAKSDIGNNVDGAQREI
DILENDPSLDADERHTAINSLVTATHGANVSLVAETAERVLESKNWKPPKNALEDLLQQK
SPPPPDVPTLVVPSPGTPGTPGTPITPGTPITPGTPITPIPGAPVTPITPTPGTPVTPVT
PGKPVTPVTPVKPGTPGEPTPITPVTPPVAPATPATPATPVTPAPAPHPQPAPAPAPSPG
PQPVTPATPGPSGPATPGTPGGEPAPHVKPAALAEQPGVPGQHAGGGTQSGPAHADESAA
SVTPAAASGVPGARAAAAAPSGTAVGAGARSSVGTAAASGAGSHAATGRAPVATSDKAAA
PSTRAASARTAPPARPPSTDHIDKPDRSESADDGTPVSMIPVSAARAARDAATAAASARQ
RGRGDALRLARRIAAALNASDNNAGDYGFFWITAVTTDGSIVVANSYGLAYIPDGMELPN
KVYLASADHAIPVDEIARCATYPVLAVQAWAAFHDMTLRAVIGTAEQLASSDPGVAKIVL
EPDDIPESGKMTGRSRLEVVDPSAAAQLADTTDQRLLDLLPPAPVDVNPPGDERHMLWFE
LMKPMTSTATGREAAHLRAFRAYAAHSQEIALHQAHTATDAAVQRVAVADWLYWQYVTGL
LDRALAAAC

FIG 1B mtbn1
1     atgactgctg aaccggaagt acggacgctg cgcgaggttg tgctggacca
51    gctcggcact gctgaatcgc gtgcgtacaa gatgtggctg ccgccgttga
101   ccaatccggt cccgctcaac gagctcatcg cccgtgatcg gcgacaaccc
151   ctgcgatttg ccctggggat catggatgaa ccgcgccgcc atctacagga
201   tgtgtggggc gtagacgttt ccggggccgg cggcaacatc ggtattgggg
251   gcgcacctca aaccgggaag tcgacgctac tgcagacgat ggtgatgtcg
301   gccgccgcca cacactcacc gcgcaacgtt cagttctatt gcatcgacct
351   aggtggcggc gggctgatct atctcgaaaa ccttccacac gtcggtgggg
401   tagccaatcg gtccgagccc gacaaggtca accgggtggt cgcagagatg
451   caagccgtca tgcggcaacg ggaaaccacc ttcaaggaac accgagtggg
501   ctcgatcggg atgtaccggc agctgcgtga cgatccaagt caacccgttg
551   cgtccgatcc atacggcgac gtctttctga tcatcgacg atggcccggt
601   tttgtcggcg agttccccga ccttgagggg caggttcaag atctggccgc
651   ccaggggctg gcgttcggcg tccacgtcat catctccacg ccacgctgga
701   cagagctgaa gtcgcgtgtt cgcgactacc tcggcaccaa gatcgagttc
751   cggcttggtg acgtcaatga aacccagatc gaccggatta cccgcgagat
801   cccggcgaat cgtccgggtc gggcagtgtc gatggaaaag caccatctga
851   tgatcggcgt gcccaggttc gacggcgtgc acagcgccga taacctggtg
901   gaggcgatca ccgcgggggt gacgcagatc gcttcccagc acaccgaaca
951   ggcacctccg gtgcgggtcc tgccggagcg tatccacctg cacgaactcg
1001  acccgaaccc gccgggacca gagtccgact accgcactcg ctgggagatt
1051  ccgatcggct gcgcgagac ggacctgacg ccggctcact gccacatgca
1101  cacgaacccg cacctactga tcttcggtgc ggccaaatcg ggcaagacga
1151  ccattgccca cgcgatcgcg cgcgccattt gtgcccgaaa cagtccccag
1201  caggtgcggt tcatgctcgc ggactaccgc tcgggcctgc tggacgcggt
1251  gccggacacc catctgctgg gcgccggcgc gatcaaccgc aacagcgcgt
1301  cgctagacga ggccgttcaa gcactggcgg tcaacctgaa gaagcggttg
1351  ccgccgaccg acctgacgac ggcgcagcta cgctcgcgtt cgtggtggag
1401  cggatttgac gtcgtgcttc tggtcgacga ttggcacatg atcgtgggtg
1451  ccgccggggg gatgccgccg atggcaccgc tggccccgtt attgccggcg
1501  gcggcagata tcgggttgca catcattgtc acctgtcaga tgagccaggc
1551  ttacaaggca accatggaca agttcgtcgg cgccgcattc gggtcgggcg
1601  ctccgacaat gttcctttcg ggcgagaagc aggaattccc atccagtgag
1651  ttcaaggtca agcggcgccc ccctggccag gcatttctcg tctcgccaga
1701  cggcaaagag gtcatccagg cccctacat cgagcctcca gaagaagtgt
1751  tcgcagcacc cccaagcgcc ggttaa mtbn2
1     atggaaaaaa tgtcacatga tccgatcgct gccgacattg cacgcaagt
51    gagcgacaac gctctgcacg gcgtgacggc cggctcgacg gcgctgacgt
101   cggtgaccgg gctggttccc gcgggggccg atgaggtctc cgcccaagcg
151   gcgacggcgt tcacatcgga gggcatccaa ttgctggctt ccaatgcatc
201   ggcccaagac cagctccacc gtgcgggcga agcggtccag gacgtcgccc
251   gcacctattc gcaaatcgac gacggcgccg ccggcgtctt cgccgaatag mtbn3
```
1    atgctgtggc acgcaatgcc accggagcta aataccgcac ggctgatggc
51   cggcgcgggt ccggctccaa tgcttgcggc ggccgcggga tggcagacgc
101  tttcggcggc tctggacgct caggccgtcg agttgaccgc gcgcctgaac
151  tctctgggag aagcctggac tggaggtggc agcgacaagg cgcttgcggc
201  tgcaacgccg atggtggtct ggctacaaac cgcgtcaaca caggccaaga
251  cccgtgcgat gcaggcgacg gcgcaagccg cggcatacac ccaggccatg
301  gccacgacgc cgtcgctgcc ggagatcgcc gccaaccaca tcacccaggc
351  cgtccttacg gccaccaact tcttcggtat caacacgatc ccgatcgcgt
401  tgaccgagat ggattatttc atccgtatgt ggaaccaggc agccctggca
451  atggaggtct accaggccga gaccgcggtt aacacgcttt cgagaagct
501  cgagccgatg gcgtcgatcc ttgatcccgg cgcgagccag agcacgacga
551  acccgatctt cggaatgccc tcccctggca gctcaacacc ggttggccag
601  ttgccgccgg cggctaccca gaccctcggc caactgggtg agatgagcgg
651  cccgatgcag cagctgaccc agccgctgca gcaggtgacg tcgttgttca
701  gccaggtggg cggcaccggc ggcggcaacc cagccgacga ggaagccgcg
751  cagatgggcc tgctcggcac cagtccgctg tcgaaccatc cgctggctgg
801  tggatcaggc ccagcgcgg gcgcgggcct gctgcgcgcg gagtcgctac
851  ctggcgcagg tgggtcgttg acccgcacgc cgctgatgtc tcagctgatc
901  gaaaagccgg ttgccccctc ggtgatgccg gcggctgctg ccggatcgtc
951  ggcgacgggt ggcgccgctc cggtgggtgc gggagcgatg ggccagggtg
1001 cgcaatccgg cggctccacc aggccgggtc tggtcgcgcc ggcaccgctc
1051 gcgcaggagc gtgaagaaga cgacgaggac gactgggacg aagaggacga
1101 ctggtga
``` mtbn4
```
1    atggcagaga tgaagaccga tgccgctacc ctcgcgcagg aggcaggtaa
51   tttcgagcgg atctccggcg acctgaaaac ccagatcgac caggtggagt
101  cgacggcagg ttcgttgcag ggccagtggc gcggcgcggc ggggacggcc
151  gcccagccg cggtggtgcg cttccaagaa gcagccaata agcagaagca
201  ggaactcgac gagatctcga cgaatattcg tcaggccggc gtccaatact
251  cgagggccga cgaggagcag cagcaggcgc tgtcctcgca aatgggcttc
301  tga
``` mtbn5
```
1    atggcggccg actacgacaa gctcttccgg ccgcacgaag gtatggaagc
51   tccggacgat atggcagcgc agccgttctt cgaccccagt gcttcgtttc
101  cgccggcgcc cgcatcggca aacctaccga agcccaacgg ccagactccg
151  cccccgacgt ccgacgacct gtcggagcgg ttcgtgtcgg ccccgccgcc
201  gccaccccca ccccacctc cgcctccgcc aactccgatg ccgatcgccg
251  caggagagcc gccctcgccg gaaccggccg catctaaacc acccacaccc
301  cccatgccca tgccggacc cgaaccggcc ccacccaaac cacccacacc
351  cccatgccc atcgccggac ccgaaccggc cccacccaaa ccacccacac
401  ctccgatgcc catcgccgga cctgcaccca ccccaaccga atcccagttg
```

FIG 2B

```
 451  gcgccccca daccaccgac accacaaacg ccaaccggag cgccgcagca
 501  accggaatca ccggcgcccc acgtaccctc gcacgggcca catcaacccc
 551  ggcgcaccgc accagcaccg ccctgggcaa agatgccaat cggcgaaccc
 601  ccgcccgctc cgtccagacc gtctgcgtcc ccggccgaac caccgacccg
 651  gcctgccccc caacactccc gacgtgcgcg ccggggtcac cgctatcgca
 701  cagacaccga acgaaacgtc gggaaggtag caactggtcc atccatccag
 751  gcgcggctgc gggcagagga agcatccggc gcgcagctcg ccccggaac
 801  ggagccctcg ccagcgccgt gggccaacc gagatcgtat ctggctccgc
 851  ccacccgccc cgcgccgaca gaacctcccc ccagcccctc gccgcagcgc
 901  aactccggtc ggcgtgccga gcgacgcgtc caccccgatt tagccgccca
 951  acatgccgcg cgcaacctg attcaattac ggccgcaacc actggcggtc
1001  gtcgccgcaa gcgtgcagcg ccggatctcg acgcgacaca gaaatcctta
1051  aggccggcg ccaaggggcc gaaggtgaag aaggtgaagc cccagaaacc
1101  gaaggccacg aagccgccca aagtggtgtc gcagcgcggc tgcgacatt
1151  gggtgcatgc gttgacgcga atcaacctgg gcctgtcacc cgacgagaag
1201  tacgagctgg acctgcacgc tcgagtccgc cgcaatcccc gcgggtcgta
1251  tcagatcgcc gtcgtcggtc tcaaaggtgg ggctggcaaa accacgctga
1301  cagcagcgtt ggggtcgacg ttggctcagg tgcgggccga ccggatcctg
1351  gctctagacg cggatccagg cgccggaaac ctcgccgatc gggtagggcg
1401  acaatcgggc gcgaccatcg ctgatgtgct tgcagaaaaa gagctgtcgc
1451  actacaacga catccgcgca cactagcg tcaatgcggt caatctggaa
1501  gtgctgccgg caccggaata cagctcggcg cagcgcgcgc tcagcgacgc
1551  cgactggcat ttcatcgccg atcctgcgtc gaggttttac aacctcgtct
1601  tggctgattg tggggccggc ttcttcgacc cgctgacccg cggcgtgctg
1651  tccacggtgt ccggtgtcgt ggtcgtggca agtgtctcaa tcgacggcgc
1701  acaacaggcg tcggtcgcgt tggactggtt gcgcaacaac ggttaccaag
1751  atttggcgag ccgcgcatgc gtggtcatca atcacatcat gccgggagaa
1801  cccaatgtcg cagttaaaga cctggtgcgg catttcgaac agcaagttca
1851  acccggccgg gtcgtggtca tgccgtggga caggcacatt gcggccggaa
1901  ccgagatttc actcgacttg ctcgacccta tctacaagcg caaggtcctc
1951  gaattggccg cagcgctatc cgacgatttc gagagggctg gacgtcgttg
2001  a
```

```
mtbn6
  1  ttgagcgcac ctgctgttgc tgctggtcct accgccgcgg gggcaaccgc
 51  tgcgcggcct gccaccaccc gggtgacgat cctgaccggc agacggatga
101  ccgatttggt actgccagcg gcggtgccga tggaaactta tattgacgac
151  accgtcgcgg tgctttccga ggtgttggaa gacacgccgg ctgatgtact
201  cggcggcttc gactttaccg cgcaaggcgt gtgggcgttc gctcgtcccg
251  gatcgccgcc gctgaagctc gaccagtcac tcgatgacgc cggggtggtc
301  gacgggtcac tgctgactct ggtgtcagtc agtcgcaccg agcgctaccg
351  accgttggtc gaggatgtca tcgacgcgat cgccgtgctt gacgagtcac
401  ctgagttcga ccgcacggca ttgaatcgct tgtggggc ggcgatcccg
451  cttttgaccg cgcccgtcat cgggatggcg atgcgggcgt ggtgggaaac
501  tgggcgtagc ttgtggtggc cgttggcgat tggcatcctg gggatcgctg
```

FIG 2C

```
 551   tgctggtagg cagcttcgtc gcgaacaggt tctaccagag cggccacctg
 601   gccgagtgcc tactggtcac gacgtatctg ctgatcgcaa ccgccgcagc
 651   gctggccgtg ccgttgccgc gcggggtcaa ctcgttgggg gcgccacaag
 701   ttgccggcgc cgctacggcc gtgctgtttt tgaccttgat gacgcggggc
 751   ggccctcgga agcgtcatga gttggcgtcg tttgccgtga tcaccgctat
 801   cgcggtcatc gcggccgccg ctgccttcgg ctatggatac caggactggg
 851   tccccgcggg ggggatcgca ttcggctgt tcattgtgac gaatgcggcc
 901   aagctgaccg tcgcggtcgc gcggatcgcg ctgccgccga ttccggtacc
 951   cggcgaaacc gtggacaacg aggagttgct cgatcccgtc gcgaccccgg
1001   aggctaccag cgaagaaacc ccgacctggc aggccatcat cgcgtcggtg
1051   cccgcgtccg cggtccggct caccgagcgc agcaaactgg ccaagcaact
1101   tctgatcgga tacgtcacgt cgggcaccct gattctggct gccggtgcca
1151   tcgcggtcgt ggtgcgcggg cacttctttg tacacagcct ggtggtcgcg
1201   ggtttgatca cgaccgtctg cggatttcgc tcgcggcttt acgccgagcg
1251   ctggtgtgcg tgggcgttgc tggcggcgac ggtcgcgatt ccgacgggtc
1301   tgacggccaa actcatcatc tggtacccgc actatgcctg gctgttgttg
1351   agcgtctacc tcacggtagc cctggttgcg ctcgtggtgg tcgggtcgat
1401   ggctcacgtc cggcgcgttt caccggtcgt aaaacgaact ctggaattga
1451   tcgacggcgc catgatcgct gccatcattc ccatgctgct gtggatcacc
1501   ggggtgtacg acacggtccg caatatccgg ttctga mtbn7
   1         atggctgaac cgttggccgt cgatcccacc ggcttgagcg cagcggccgc
  51   gaaattggcc ggcctcgttt ttccgcagcc tccggcgccg atcgcggtca
 101   gcggaacgga ttcggtggta gcagcaatca acgagaccat gccaagcatc
 151   gaatcgctgg tcagtgacgg gctgcccggc gtgaaagccg ccctgactcg
 201   aacagcatcc aacatgaacg cggcggcgga cgtctatgcg aagaccgatc
 251   agtcactggg aaccagtttg agccagtatg cattcggctc gtcgggcgaa
 301   ggcctggctg gcgtcgcctc ggtcggtggt cagccaagtc aggctaccca
 351   gctgctgagc acaccgtgt cacaggtcac gacccagctc ggcgagacgg
 401   ccgctgagct ggcaccccgt gttgttgcga cggtgccgca actcgttcag
 451   ctggctccgc acgccgttca gatgtcgcaa aacgcatccc ccatcgctca
 501   gacgatcagt caaaccgccc aacaggccgc ccagagcgcg cagggcggca
 551   gcggcccaat gcccgcacag cttgccagcg ctgaaaaacc ggccaccgag
 601   caagcggagc cggtccacga agtgacaaac gacgatcagg gcgaccaggg
 651   cgacgtgcag ccggccgagg tcgttgccgc ggcacgtgac gaaggcgccg
 701   gcgcatcacc gggccagcag cccggcgggg gcgttcccgc gcaagccatg
 751   gataccggag ccggtgcccg cccagcggcg agtccgctgg cggccccgt
 801   cgatccgtcg actccggcac cctcaacaac cacaacgttg tag
```

FIG 2D mtbn8

```
1    atgagtatta ccaggccgac gggcagctat gccagacaga tgctggatcc
51   gggcggctgg gtggaagccg atgaagacac tttctatgac cgggcccagg
101  aatatagcca ggttttgcaa agggtcaccg atgtattgga cacctgccgc
151  cagcagaaag gccacgtctt cgaaggcggc ctatggtccg gcggcgccgc
201  caatgctgcc aacggcgccc tgggtgcaaa catcaatcaa ttgatgacgc
251  tgcaggatta tctcgccacg gtgattacct ggcacaggca tattgccggg
301  ttgattgagc aagctaaatc cgatatcggc aataatgtgg atggcgctca
351  acgggagatc gatatcctgg agaatgaccc tagcctggat gctgatgagc
401  gccataccgc catcaattca ttggtcacgg cgacgcatgg ggccaatgtc
451  agtctggtcg ccgagaccgc tgagcgggtg ctggaatcca agaattggaa
501  acctccgaag aacgcactcg aggatttgct tcagcagaag tcgccgccac
551  ccccagacgt gcctaccctg gtcgtgccat ccccgggcac accgggcaca
601  ccgggaaccc cgatcacccc gggaaccccg atcacccgg gaaccccaat
651  cacacccatc ccgggagcgc cggtaactcc gatcacacca acgcccggca
701  ctcccgtcac gccggtgacc ccgggcaagc cggtcacccc ggtgaccccg
751  gtcaaaccgg gcacaccagg cgagccaacc ccgatcacgc cggtcacccc
801  cccggtcgcc ccggccacac cggcaacccc ggccacgccc gttacccag
851  ctcccgctcc acaccgcag ccggctccgg caccggcgcc atcgcctggg
901  ccccagccgg ttacaccggc cactcccggt ccgtctggtc cagcaacacc
951  gggcacccca ggggcgagc cggcgccgca cgtcaaaccc gcggcgttgg
1001 cggagcaacc tggtgtgccg ggccagcatg cgggcggggg gacgcagtcg
1051 gggcctgccc atgcggacga atccgccgcg tcggtgacgc cggctgcggc
1101 gtccggtgtc ccgggcgcac gggcggcggc cgccgcgccg agcggtaccg
1151 ccgtgggagc gggcgcgcgt tcgagcgtgg gtacggccgc ggcctcgggc
1201 gcgggtcgc atgctgccac tgggcgggcg ccggtggcta cctcggacaa
1251 ggcggcggca ccgagcacgc gggcggcctc ggcgcggacg gcacctcctg
1301 cccgcccgcc gtcgaccgat cacatcgaca aacccgatcg cagcgagtct
1351 gcagatgacg gtacgccggt gtcgatgatc ccggtgtcgg cggctcgggc
1401 ggcacgcgac gccgccactg cagctgccag cgcccgccag cgtggccgcg
1451 gtgatgcgct gcggttggcg cgacgcatcg cggcggcgct caacgcgtcc
1501 gacaacaacg cgggcgacta cgggttcttc tggatcaccg cggtgaccac
1551 cgacggttcc atcgtcgtgg ccaacagcta tgggctggcc tacatacccg
1601 acgggatgga attgccgaat aaggtgtact ggccagcgc ggatcacgca
1651 atcccggttg acgaaattgc acgctgtgcc acctacccgg ttttggccgt
1701 gcaagcctgg gcggctttcc acgacatgac gctgcgggcg gtgatcggta
1751 ccgcggagca gttggccagt tcggatcccg gtgtggccaa gattgtgctg
1801 gagccagatg acattccgga gagcggcaaa atgacgggcc ggtcgcggct
1851 ggaggtcgtc gacccctcgg cggcggctca gctggccgac actaccgatc
1901 agcgtttgct cgacttgttg ccgccggcgc cggtggatgt caatccaccg
1951 ggcgatgagc ggcacatgct gtggttcgag ctgatgaagc ccatgaccag
2001 caccgctacc ggccgcgagg ccgctcatct gcgggcgttc cgggcctacg
2051 ctgcccactc acaggagatt gccctgcacc aagcgcacac tgcgactgac
2101 gcggccgtcc agcgtgtggc cgtcgcggac tggctgtact ggcaatacgt
2151 caccgggttg ctcgaccggg ccctggccgc cgcatgctga
```

PROTEINS EXPRESSED BY MYCOBACTERIUM TUBERCULOSIS AND NOT BY BCG AND THEIR USE AS DIAGNOSTIC REAGENTS AND VACCINES

This application is a divisional of, and claims priority to, U.S. application Ser. No. 13/198,108, filed Aug. 4, 2011 and now pending, which is a continuation of, and claims priority to, U.S. application Ser. No. 12/503,717, filed Jul. 15, 2009 and now issued as U.S. Pat. No. 8,021,832, which is a continuation of, and claims priority to, U.S. application Ser. No. 11/677,502, filed Feb. 21, 2007, now U.S. Pat. No. 7,579,141, which is a divisional of, and claims priority to, U.S. application Ser. No. 10/009,383, filed Mar. 4, 2002 and now issued as U.S. Pat. No. 7,932,373, which claims priority to International Application No. PCT/US00/12257, filed May 4, 2000, which claims priority to U.S. Provisional Application Ser. No. 60/132,505, filed May 4, 1999, the disclosures of each of which are hereby incorporated by reference in their entireties.

BACKGROUND OF THE INVENTION

Tuberculosis infection continues to be a world-wide health problem. This situation has recently been greatly exacerbated by the emergence of multi-drug resistant strains of *M. tuberculosis* and the international AIDS epidemic. It has thus become increasingly important that effective vaccines against and reliable diagnostic reagents for *M. tuberculosis* be produced.

The disclosure of U.S. Pat. No. 6,087,163 is incorporated herein by reference in its entirety.

SUMMARY OF THE INVENTION

The invention is based on the inventor's discovery that a polypeptide encoded by an open reading frame (ORF) in the genome of *M. tuberculosis* that is absent from the genome of the Bacille Calmette Guerin (BCG) strain of *M. bovis* elicited a delayed-type hypersensitivity response in animals infected with *M. tuberculosis* but not in animals sensitized with BCG. Thus proteins encoded by ORFs present in the genome of *M. tuberculosis* but absent from the genome of BCG represent reagents that are useful in discriminating between *M. tuberculosis* and BCG and, in particular, for diagnostic methods (e.g., skin tests and in vitro assays for *M. tuberculosis*-specific antibodies and lymphocyte responsiveness) which discriminate between exposure of a subject to *M. tuberculosis* and vaccination with BCG. The invention features these polypeptides, functional segments thereof, DNA molecules encoding either the polypeptides or the functional segments, vectors containing the DNA molecules, cells transformed by the vectors, compositions containing one or more of any of the above polypeptides, functional segments, or DNA molecules, and a variety of diagnostic, therapeutic, and prophylactic (vaccine) methodologies utilizing the foregoing.

Specifically, the invention features an isolated DNA molecule containing a DNA sequence encoding a polypeptide with a first amino acid sequence that can be the amino acid sequence of the polypeptide MTBN1, MTBN2, MTBN3, MTBN4, MTBN5, MTBN6, MTBN7 or MTBN8, as depicted in FIGS. 1A and 1B, or a second amino acid sequence identical to the first amino acid sequence with conservative substitutions; the polypeptide has *Mycobacterium tuberculosis* specific antigenic and immunogenic properties. Also included in the invention is an isolated portion of the above DNA molecule. The portion of the DNA molecule encodes a segment of the polypeptide shorter than the full-length polypeptide, and the segment has *Mycobacterium tuberculosis* specific antigenic and immunogenic properties. Other embodiments of the invention are vectors containing the above DNA molecules and transcriptional and translational regulatory sequences operationally linked to the DNA sequence; the regulatory sequences allow for expression of the polypeptide or functional segment encoded by the DNA sequence in a cell. The invention encompasses cells (e.g., eukaryotic and prokaryotic cells) transformed with the above vectors.

The invention encompasses compositions containing any of the above vectors and a pharmaceutically acceptable diluent or filler. Other compositions (to be used, for example, as DNA vaccines) can contain at least two (e.g., three, four, five, six, seven, eight, nine, ten, twelve, fifteen, or twenty) DNA sequences, each encoding a polypeptide of the *Mycobacterium tuberculosis* complex or a functional segment thereof, with the DNA sequences being operationally linked to transcriptional and translational regulatory sequences which allow for expression of each of the polypeptides in a cell of a vertebrate. In such compositions, at least one (e.g., two, three, four, five, six, seven, or eight) of the DNA sequences is one of the above DNA molecules of the invention. The encoded polypeptides will preferably be those not encoded by the genome of cells of the BCG strain of *M. bovis*.

The invention also features an isolated polypeptide with a first amino acid sequence that can be the sequence of the polypeptide MTBN1, MTBN2, MTBN3, MTBN4, MTBN5, MTBN6, MTBN7 or MTBN8 as depicted in FIGS. 1A and 1B, or a second amino acid sequence identical to the first amino acid sequence with conservative substitutions. The polypeptide has *Mycobacterium tuberculosis* specific antigenic and immunogenic properties. Also included in the invention is an isolated segment of this polypeptide, the segment being shorter than the full-length polypeptide and having *Mycobacterium tuberculosis* specific antigenic and immunogenic properties. Other embodiments are compositions containing the polypeptide, or functional segment, and a pharmaceutically acceptable diluent or filler. Compositions of the invention can also contain at least two (e.g., three, four, five, six, seven, eight, nine, ten, twelve, fifteen, or twenty) polypeptides of the *Mycobacterium tuberculosis* complex, or functional segments thereof, with at least one of the at least two (e.g., two, three, four, five, six, seven, or eight) polypeptides having the sequence of one of the above described polypeptides of the invention. The polypeptides will preferably be those not encoded by the genome of cells of the BCG strain of *M. bovis*.

The invention also features methods of diagnosis. One embodiment is a method involving: (a) administration of one of the above polypeptide compositions to a subject suspected of having or being susceptible to *Mycobacterium tuberculosis* infection; and (b) detecting an immune response in the subject to the composition, as an indication that the subject has or is susceptible to *Mycobacterium tuberculosis* infection. An example of such a method is a skin test in which the test substance (e.g., compositions containing one or more of MTBN1-MTBN8) is injected intradermally into the subject and in which a skin delayed-type hypersensitivity response is tested for. Another embodiment is a method that involves: (a) providing a population of cells containing CD4 T lymphocytes from a subject; (b) providing a population of cells containing antigen presenting cells (APC) expressing a major histocompatibility complex (MHC) class II molecule expressed by the subject; (c) contacting the CD4 lymphocytes of (a) with the APC of (b) in the presence of one or more of the polypeptides, functional segments, and or polypeptide compositions of the invention; and (d) determining the ability of the CD4 lymphocytes to respond to the polypeptide, as an indication that the subject has or is susceptible to *Mycobacterium tuberculosis* infection. Another diagnostic method of the invention involves: (a) contacting a polypeptide, a functional segment, or a polypeptide/functional segment composition of the invention with a bodily fluid of a subject; (b) detecting the presence of binding of antibody to the polypeptide, functional segment, or polypeptide/functional segment composition, as an indication that the subject has or is susceptible to *Mycobacterium tuberculosis* infection.

Also encompassed by the invention are methods of vaccination. These methods involve administration of any of the above polypeptides, functional segments, or DNA compositions to a subject. The compositions can be administered alone or with one or more of the other compositions.

As used herein, an "isolated DNA molecule" is a DNA which is one or both of: not immediately contiguous with one or both of the coding sequences with which it is immediately contiguous (i.e., one at the 5' end and one at the 3' end) in the naturally-occurring genome of the organism from which the DNA is derived; or which is substantially free of DNA sequence with which it occurs in the organism from which the DNA is derived. The term includes, for example, a recombinant DNA which incorporated into a vector, e.g., into an autonomously replicating plasmid or virus, or into the genomic DNA of a prokaryote or eukaryote, or which exists as a separate molecule (e.g., a cDNA or a genomic fragment produced by PCR or restriction endonuclease treatment) independent of other DNA sequences. Isolated DNA also includes a recombinant DNA which is part of a hybrid DNA encoding additional *M. tuberculosis* polypeptide sequences.

"DNA molecules" include cDNA, genomic DNA, and synthetic (e.g., chemically synthesized) DNA. Where single-stranded, the DNA molecule may be a sense strand or an antisense strand.

An "isolated polypeptide" of the invention is a polypeptide which either has no naturally-occurring counterpart, or has been separated or purified from components which naturally accompany it, e.g., in *M. tuberculosis* bacteria. Typically, the polypeptide is considered "isolated" when it is at least 70%, by dry weight, free from the proteins and naturally-occurring organic molecules with which it is naturally associated. Preferably, a preparation of a polypeptide of the invention is at least 80%, more preferably at least 90%, and most preferably at least 99%, by dry weight, the peptide of the invention. Since a polypeptide that is chemically synthesized is, by its nature, separated from the components that naturally accompany it, the synthetic polypeptide is "isolated."

An isolated polypeptide of the invention can be obtained, for example, by extraction from a natural source (e.g., *M. tuberculosis* bacteria); by expression of a recombinant nucleic acid encoding the polypeptide; or by chemical synthesis. A polypeptide that is produced in a cellular system different from the source from which it naturally originates is "isolated," because it will be separated from components which naturally accompany it. The extent of isolation or purity can be measured by any appropriate method, e.g., column chromatography, polyacrylamide gel electrophoresis, or HPLC analysis.

The polypeptides may contain a primary amino acid sequence that has been modified from those disclosed herein. Preferably these modifications consist of conservative amino acid substitutions. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

The terms "protein" and "polypeptide" are used herein to describe any chain of amino acids, regardless of length or post-translational modification (for example, glycosylation or phosphorylation). Thus, the term "*Mycobacterium tuberculosis* polypeptide" includes full-length, naturally occurring *Mycobacterium tuberculosis* protein, as well a recombinantly or synthetically produced polypeptide that corresponds to a full-length naturally occurring *Mycobacterium tuberculosis* protein or to particular domains or portions of a naturally occurring protein. The term also encompasses a mature *Mycobacterium tuberculosis* polypeptide which has an added amino-terminal methionine (useful for expression in prokaryotic cells) or any short amino acid sequences useful for protein purification by affinity chromatography, e.g., polyhistidine for purification by metal chelate chromatography.

As used herein, "immunogenic" means capable of activating a primary or memory immune response. Immune responses include responses of CD4+ and CD8+ T lymphocytes and B-lymphocytes. In the case of T lymphocytes, such responses can be proliferative, and/or cytokine (e.g., interleukin (IL)-2, IL-3, IL-4, IL-5, IL-6, IL-12, IL-13, IL-15, tumor necrosis factor-a (TNF-a), or interferon-y (IFN-y))-producing, or they can result in generation of cytotoxic T-lymphocytes (CTL). B-lymphocyte responses can be those resulting in antibody production by the responding B lymphocytes.

As used herein, "antigenic" means capable of being recognized by either antibody molecules or antigen-specific T cell receptors (TCR) on activated effector T cells (e.g., cytokine-producing T cells or CTL).

Thus, polypeptides that have "*Mycobacterium tuberculosis* specific antigenic properties" are polypeptides that: (a) can be recognized by and bind to antibodies elicited in response to *Mycobacterium tuberculosis* organisms or wild-type *Mycobacterium tuberculosis* molecules (e.g., polypeptides); or (b) contain subsequences which, subsequent to processing of the polypeptide by appropriate antigen presenting cells (APC) and bound to appropriate major histocompatibility complex (MHC) molecules, are recognized by and bind to TCR on effector T cells elicited in response to *Mycobacterium tuberculosis* organisms or wild-type *Mycobacterium tuberculosis* molecules (e.g., polypeptides).

As used herein, polypeptides that have "*Mycobacterium tuberculosis* specific immunogenic properties" are polypeptides that: (a) can elicit the production of antibodies that recognize and bind to *Mycobacterium tuberculosis* organisms or wild-type *Mycobacterium tuberculosis* molecules (e.g., polypeptides); or (b) contain subsequences which, subsequent to processing of the polypeptide by appropriate antigen presenting cells (APC) and bound to appropriate major histocompatibility complex (MHC) molecules on the surface of the APC, activate T cells with TCR that recognize and bind to peptide fragments derived by processing by APC of *Mycobacterium tuberculosis* organisms or wild-type *Mycobacterium tuberculosis* molecules (e.g., polypeptides) and bound to MHC molecules on the surface of the APC. The immune responses elicited in response to the immunogenic polypeptides are preferably protective. As used herein, "protective" means preventing establishment of an infection or onset of a disease or lessening the severity of a disease existing in a subject. "Preventing" can include delaying onset, as well as partially or completely blocking progress of the disease.

As used herein, a "functional segment of a *Mycobacterium tuberculosis* polypeptide" is a segment of the polypeptide that has *Mycobacterium tuberculosis* specific antigenic and immunogenic properties.

Where a polypeptide, functional segment of a polypeptide, or a mixture of polypeptides and/or functional segments have been administered (e.g., by intradermal injection) to a subject for the purpose of testing for a *M. tuberculosis* infection or susceptibility to such an infection, "detecting an immune response" means examining the subject for signs of an immunological reaction to the administered material, e.g., reddening or swelling of the skin at the site of an intradermal injection. Where the subject has antibodies to the administered material, the response will generally be rapid, e.g., 1 minute to 24 hours. On the other hand, a memory or activated T cell reaction of pre-immunized T lymphocytes in the subject is generally slower, appearing only after 24 hours and being maximal at 24-96 hours.

As used herein, a "subject" can be a human subject or a non-human mammal such as a non-human primate, a horse, a bovine animal, a pig, a sheep, a goat, a dog, a cat, a rabbit, a guinea pig, a hamster, a rat, or a mouse.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. Unless otherwise indicated, these materials and methods are illustrative only and are not intended to be limiting.

All publications, patent applications, patents and other references mentioned herein are illustrative only and not intended to be limiting.

Other features and advantages of the invention, e.g., methods of diagnosing *M. tuberculosis* infection, will be apparent from the following description, from the drawings and from the claims.

BRIEF DESCRIPTION OF THE DRAWINGS

FIGS. 1A and 1B are a depiction of the amino acid sequences of *M. tuberculosis* polypeptides MTBN1-MTBN8 (SEQ ID NOS:1-8, respectively).

FIGS. 2A-2E are a depiction of the nucleotide sequences of the coding regions (mtbn1-mtbn8) encoding MTBN1-MTBN8 (SEQ ID NOS:9-16, respectively).

DETAILED DESCRIPTION

Figure 3:
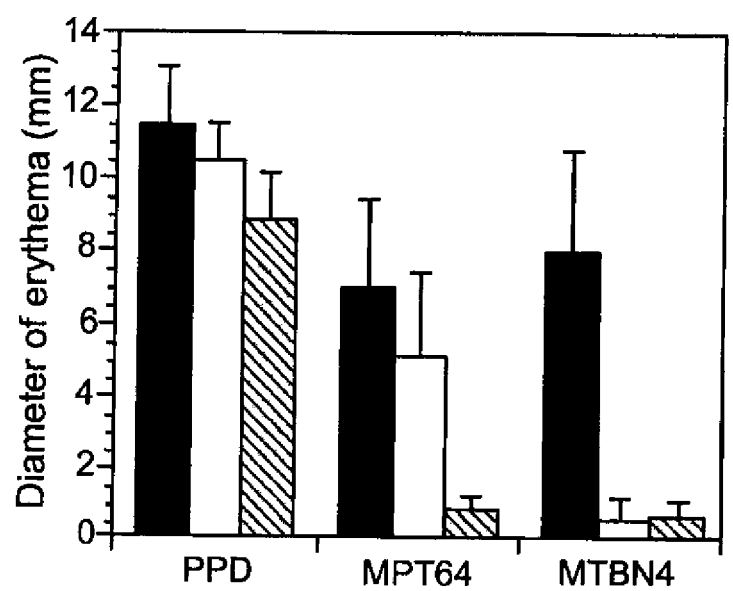
FIG. 3 is a bar graph showing the delayed-type hypersensitivity responses induced by intradermal injection of 3 different test reagents in female guinea pigs that had been either infected with *M. tuberculosis* cells or sensitized with BCG or *M. avium* cells.

The genome of *M. tuberculosis* [Cole et al. (1998) Nature 393: 537-544] contains open reading frames (ORFs) that have been deleted from the avirulent BCG strain.

The polypeptides encoded by these ORFs are designated herein "*M. tuberculosis* BCG Negative" polypeptides ("MTBN") and the ORFs are designated "mtbn." The invention is based on the discovery that a MTBN polypeptide (MTBN4) elicited a skin response in animals infected with *M. tuberculosis*, but not in animals sensitized to either BCG or *M. avium*, a non-*M. tuberculosis*-complex strain of mycobacteria (see Example 1 below). These findings indicate that MTBN (e.g., MTBN1-MTBN8) can be used in diagnostic tests that discriminate infection of a subject by *M. tuberculosis* from exposure to both mycobacteria other than the *M. tuberculosis*-complex and BCG. The *M. tuberculosis*-complex includes *M. tuberculosis, M. bovis, M. microti*, and *M. africanum*. Thus they can be used to discriminate subjects exposed to *M. tuberculosis*, and thus potentially having or being in danger of having tuberculosis, from subjects that have been vaccinated with BCG, the most widely used tuberculosis vaccine. Diagnostic assays that are capable of such discrimination represent a major advance that will greatly reduce wasted effort and consequent costs resulting from further diagnostic tests and/or therapeutic procedures in subjects that have given positive results in less discriminatory diagnostic tests.

Furthermore, the results in Example 1 show that MTBN4, as expressed by whole viable *M. tuberculosis* organisms, is capable of inducing a strong immune response in subjects infected with the organisms and thus has the potential to be a vaccine.

The MTBN polypeptides of the invention include, for example, polypeptides encoded within the RD1, RD2, and RD3 regions of the *M. tuberculosis* genome [Mahairas et al. (1996) J. Bacteriol. 178: 1274-1282]. Of particular interest are polypeptides encoded by ORFs within the RD1 region of the *M. tuberculosis* genome. However, the invention is not restricted to the RD 1, RD2, and RD3 region encoded polypeptides and includes any polypeptides encoded by ORFs contained in the genome of one or more members of the *M. tuberculosis* genome and not contained in the genome of BCG. The amino acid sequences of MTBN1-MTBN8 are shown in FIGS. 1A and 1B and the nucleotide sequences of mtbn1-mtbn8 are shown in FIGS. 2A-2E.

The invention encompasses: (a) isolated DNA molecules containing mtbn sequences (e.g., mtbn1-mtbn8) encoding MTBN polypeptides (e.g., MTBN1-MTBN8) and isolated portions of such DNA molecules that encode polypeptide segments having antigenic and immunogenic properties (i.e., functional segments); (b) the MTBN polypeptides themselves (e.g., MTBN1-MTBN8) and functional segments of them; (c) antibodies (including antigen binding fragments, e.g., F (ab') 2, Fab, Fv, and single chain Fv fragments of such antibodies) that bind to the MTBN polypeptides (e.g., MTBN1-MTBN8) and functional segments; (d) nucleic acid molecules (e.g., vectors) containing and capable of expressing one or more of the mtbn (e.g., mtbn1-mtbn8) sequences and portions of DNA molecules; (e) cells (e.g., bacterial, yeast, insect, or mammalian cells) transformed by such vectors; (f) compositions containing vectors encoding one or more *M. tuberculosis* polypeptides (or functional segments) including both the MTBN (e.g., MTBN1-MTBN8) polypeptides (or functional segments thereof) and previously described *M. tuberculosis* polypeptides such as ESAT-6, 14 kDa antigen, MPT63, 19 kDa antigen, MPT64, MPT51, MTC28, 38 kDa antigen, 45/47 kDa antigen, MPB70, Ag85 complex, MPT53, and KatG (see also U.S. Pat. No. 6,087, 163); (g) compositions containing one or more *M. tuberculosis* polypeptides (or functional segments), including both the polypeptides of the invention and previously described *M. tuberculosis* polypeptides such as those described above; (h) compositions containing one or more of the antibodies described in (c); (i) methods of diagnosis involving either (1) administration (e.g., intradermal injection) of any of the above polypeptide compositions to a subject suspected of having or being susceptible to *M. tuberculosis* infection, (2) in vitro testing of lymphocytes (B-lymphocytes, CD4 T lymphocytes, and CD8 T lymphocytes) from such a subject for responsiveness (e.g., by measuring cell proliferation, antibody production, cytokine production, or CTL activity) to any of the above polypeptide compositions, (3) testing of a bodily fluid (e.g., blood, saliva, plasma, serum, urine, or semen or a lavage such as a bronchoalveolar lavage, a vaginal lavage, or lower gastrointestinal lavage) for antibodies to the MTBN polypeptides (e.g., MTBN1-MTBN8) or functional segments thereof, or the above-described polypeptide compositions; (4) testing of a bodily fluid (e.g., as above) for the presence of M. tuberculosis, MTBN (e.g., MTBN1-MTBN8) polypeptides or functional segments thereof, or the above-described polypeptide compositions in assays using the antibodies described in (c); and (5) testing of a tissue (e.g. lung or bronchial tissue) or a body fluid (e.g., as above) for the presence of nucleic acid molecules (e.g., DNA or RNA) encoding MTBN polypeptides (e.g., MTBN1-MTBN8) (or portions of such a nucleic acid molecules) using nucleic acid probes or primers having nucleotide sequences of the nucleic molecules, portions of the nucleic molecules, or the complements of such molecules; and (j) methods of vaccination involving administration to a subject of the compositions of either (f), (g), (h) or a combination of any two or even all 3 compositions.

With respect to diagnosis, purified MTBN proteins, functional segments of such proteins, or mixtures of proteins and/or the functional fragments have the above-described advantages of discriminating infection by M. tuberculosis from either infection by other bacteria, and in particular, non-pathogenic mycobacteria, or from exposure (by, for example, vaccination) to BCG.

Furthermore, compositions containing the proteins, functional segments of the proteins, or mixtures of the proteins and/or the functional segments allows for improved quality control since "batch-to-batch" variability is greatly reduced in comparison to complex mixtures such as purified protein derivative (PPD) of tuberculin.

The use of the above-described polypeptide and nucleic acid reagents for vaccination also provides for highly specific and effective immunization. Since the virulent M. tuberculosis polypeptides encoded by genes absent from avirulent BCG are likely to be mediators of virulence, immunity directed to them can be especially potent in terms of protective capacity. Where vaccination is performed with nucleic acids both in vivo and ex vivo methods can be used. In vivo methods involve administration of the nucleic acids themselves to the subject and ex vivo methods involve obtaining cells (e.g., bone marrow cells or fibroblasts) from the subject, transducing the cells with the nucleic acids, preferably selecting or enriching for successfully transduced cells, and administering the transduced cells to the subject. Alternatively, the cells that are transduced and administered to the subject can be derived from another subject. Methods of vaccination and diagnosis are described in greater detail in U.S. Pat. No. 6,087,163, the disclosure of which is incorporated herein by reference in its entirety.

The following example is meant to illustrate, not limit the invention.

Example 1

MTBN4 Elicits a Specific Skin Reaction in Guinea Pigs Infected with M. tuberculosis Four groups of outbred female guinea pigs (18 per group) were used to test the usefulness of the MTBN4 polypeptide as a M. tuberculosis-specific diagnostic reagent. The four groups were treated as follows.

Group 1 animals were infected by aerosol with approximately 100 M. tuberculosis strain H37Rv cells.

Group 2 animals were sensitized intradermally with 106 live M. bovis BCG Japanese cells.

Group 3 animals were sensitized intradermally with 106 live M. avium cells.

Group 4 animals were mock-sensitized by intradermal injection with saline.

Seven weeks after infection or sensitization, the animals were injected intradermally with 1 μg of PPD (6 animals from each group), 2 μg of purified recombinant MPT64 (6 animals from each group), or 2 μg of MTBN4 (6 animals from each group). The diameter of the resulting erythema was measured 24 hours later. Data are expressed as mean diameter of erythema (in mm) and standard deviations are indicated (FIG. 3).

No erythema was detected in the group 4 animals with any test substance and thus no data are shown for this group. On the other hand, group 1 animals (solid bars) showed a significant response with all three test substances. Group 2 animals (open bars) showed a significant response to PPD and MPT64 but not MTBN4.

Group 3 animals showed a significant response to PPD only (hatched bars).

Thus, PPD which contains antigenic/immunogenic molecules common to the M. tuberculosis-complex as well as other mycobacterial strains, gave the least discriminatory results in that it induced responses in animals infected with or sensitized to mycobacteria of the M. tuberculosis-complex (M. tuberculosis and BCG) as well as another non-pathogenic mycobacterium (M. avium).

While MPT64, which is encoded and expressed by both M. tuberculosis and BCG, did not elicit a response in animals infected with M. avium, it did elicit responses in both the M. tuberculosis infected and the BCG sensitized animals. Finally, MTBN4 elicited a response in only the M. tuberculosis animals. Thus it induced the most specific response and, most importantly, allowed for discrimination between animals infected with M. tuberculosis and those sensitized to BCG.

Although the invention has been described with reference to the presently preferred embodiment, it should be understood that various modifications can be made without departing from the spirit of the invention. Accordingly, the invention is limited only by the following claims.

What is claimed is:

1. A diagnostic composition that discriminates between infection by *Mycobacterium tuberculosis* and vaccination by Bacille Calmette Guerin (BCG) strain of *Mycobacterium bovis*, said composition comprising antigens, all antigens in said composition consisting of at least three different polypeptides of the *Mycobacterium tuberculosis* complex that are not encoded by BCG, and said polypeptides including at least one isolated polypeptide from the group consisting of (i) a first amino acid sequence consisting of the sequence of MTBN4 (SEQ ID NO: 4), (ii) a second amino acid sequence that is an antigenic segment of MTBN4 that has *Mycobacterium tuberculosis* specific antigenic or immunogenic properties and (iii) a third amino acid sequence that is identical to said first or second amino acid sequence but has conservative substitutions and has *Mycobacterium tuberculosis* specific antigenic or immunogenic properties.

2. The composition of claim 1, wherein said at least one isolated polypeptide comprises consists of said first or second amino acid sequence.

3. The composition of claim 2 further including a pharmaceutically acceptable diluent or filler.

4. The composition of claim 1 further including a pharmaceutically acceptable diluent or filler.

5. A mixture of a composition of claim 1 and a bodily fluid.

6. The mixture of claim 5, wherein the bodily fluid is blood, saliva, plasma, serum, urine, semen, or a lavage.

7. The composition mixture of claim 6, wherein the lavage is a bronchoalveolar lavage, a vaginal lavage, or lower gastrointestinal lavage.

* * * * *

UNITED STATES PATENT AND TRADEMARK OFFICE
CERTIFICATE OF CORRECTION

PATENT NO.        : 8,974,800 B2  
APPLICATION NO.   : 13/893659  
DATED             : March 10, 2015  
INVENTOR(S)       : Maria L. Gennaro Page 1 of 1

It is certified that error appears in the above-identified patent and that said Letters Patent is hereby corrected as shown below:

In the Claims:

At column 50, claim number 2, line number 48, delete "comprises"

Signed and Sealed this
Nineteenth Day of July, 2016

Michelle K. Lee
*Director of the United States Patent and Trademark Office*

SEQUENCE LISTING

<160> NUMBER OF SEQ ID NOS: 16

<210> SEQ ID NO 1
<211> LENGTH: 591
<212> TYPE: PRT
<213> ORGANISM: Mycobacterium tuberculosis

<400> SEQUENCE: 1

Met Thr Ala Glu Pro Glu Val Arg Thr Leu Arg Glu Val Val Leu Asp

-continued

```
  1               5                    10                   15
Gln Leu Gly Thr Ala Glu Ser Arg Ala Tyr Lys Met Trp Leu Pro Pro
                20                  25                  30

Leu Thr Asn Pro Val Pro Leu Asn Glu Leu Ile Ala Arg Asp Arg Arg
                35                  40                  45

Gln Pro Leu Arg Phe Ala Leu Gly Ile Met Asp Glu Pro Arg Arg His
        50                  55                  60

Leu Gln Asp Val Trp Gly Val Asp Val Ser Gly Ala Gly Gly Asn Ile
65                  70                  75                  80

Gly Ile Gly Gly Ala Pro Gln Thr Gly Lys Ser Thr Leu Leu Gln Thr
                85                  90                  95

Met Val Met Ser Ala Ala Ala Thr His Ser Pro Arg Asn Val Gln Phe
                100                 105                 110

Tyr Cys Ile Asp Leu Gly Gly Gly Leu Ile Tyr Leu Glu Asn Leu
                115                 120                 125

Pro His Val Gly Gly Val Ala Asn Arg Ser Glu Pro Asp Lys Val Asn
        130                 135                 140

Arg Val Val Ala Glu Met Gln Ala Val Met Arg Gln Arg Glu Thr Thr
145                 150                 155                 160

Phe Lys Glu His Arg Val Gly Ser Ile Gly Met Tyr Arg Gln Leu Arg
                165                 170                 175

Asp Asp Pro Ser Gln Pro Val Ala Ser Asp Pro Tyr Gly Asp Val Phe
        180                 185                 190

Leu Ile Ile Asp Gly Trp Pro Gly Phe Val Gly Glu Phe Pro Asp Leu
        195                 200                 205

Glu Gly Gln Val Gln Asp Leu Ala Ala Gln Gly Leu Ala Phe Gly Val
        210                 215                 220

His Val Ile Ile Ser Thr Pro Arg Trp Thr Glu Leu Lys Ser Arg Val
225                 230                 235                 240

Arg Asp Tyr Leu Gly Thr Lys Ile Glu Phe Arg Leu Gly Asp Val Asn
                245                 250                 255

Glu Thr Gln Ile Asp Arg Ile Thr Arg Glu Ile Pro Ala Asn Arg Pro
                260                 265                 270

Gly Arg Ala Val Ser Met Glu Lys His His Leu Met Ile Gly Val Pro
        275                 280                 285

Arg Phe Asp Gly Val His Ser Ala Asp Asn Leu Val Glu Ala Ile Thr
        290                 295                 300

Ala Gly Val Thr Gln Ile Ala Ser Gln His Thr Glu Gln Ala Pro Pro
305                 310                 315                 320

Val Arg Val Leu Pro Glu Arg Ile His Leu His Glu Leu Asp Pro Asn
                325                 330                 335

Pro Pro Gly Pro Glu Ser Asp Tyr Arg Thr Arg Trp Glu Ile Pro Ile
        340                 345                 350

Gly Leu Arg Glu Thr Asp Leu Thr Pro Ala His Cys His Met His Thr
        355                 360                 365

Asn Pro His Leu Leu Ile Phe Gly Ala Ala Lys Ser Gly Lys Thr Thr
        370                 375                 380

Ile Ala His Ala Ile Ala Arg Ala Ile Cys Ala Arg Asn Ser Pro Gln
385                 390                 395                 400

Gln Val Arg Phe Met Leu Ala Asp Tyr Arg Ser Gly Leu Leu Asp Ala
                405                 410                 415

Val Pro Asp Thr His Leu Leu Gly Ala Gly Ala Ile Asn Arg Asn Ser
                420                 425                 430
```

-continued

```
Ala Ser Leu Asp Glu Ala Val Gln Ala Leu Ala Val Asn Leu Lys Lys
        435                 440                 445

Arg Leu Pro Pro Thr Asp Leu Thr Thr Ala Gln Leu Arg Ser Arg Ser
450                 455                 460

Trp Trp Ser Gly Phe Asp Val Val Leu Leu Val Asp Asp Trp His Met
465                 470                 475                 480

Ile Val Gly Ala Ala Gly Gly Met Pro Pro Met Ala Pro Leu Ala Pro
                485                 490                 495

Leu Leu Pro Ala Ala Asp Ile Gly Leu His Ile Ile Val Thr Cys
                500                 505                 510

Gln Met Ser Gln Ala Tyr Lys Ala Thr Met Asp Lys Phe Val Gly Ala
                515                 520                 525

Ala Phe Gly Ser Gly Ala Pro Thr Met Phe Leu Ser Gly Glu Lys Gln
            530                 535                 540

Glu Phe Pro Ser Ser Glu Phe Lys Val Lys Arg Arg Pro Pro Gly Gln
545                 550                 555                 560

Ala Phe Leu Val Ser Pro Asp Gly Lys Glu Val Ile Gln Ala Pro Tyr
                565                 570                 575

Ile Glu Pro Pro Glu Glu Val Phe Ala Ala Pro Pro Ser Ala Gly
                580                 585                 590

<210> SEQ ID NO 2
<211> LENGTH: 99
<212> TYPE: PRT
<213> ORGANISM: Mycobacterium tuberculosis

<400> SEQUENCE: 2

Met Glu Lys Met Ser His Asp Pro Ile Ala Ala Asp Ile Gly Thr Gln
1               5                   10                  15

Val Ser Asp Asn Ala Leu His Gly Val Thr Ala Gly Ser Thr Ala Leu
                20                  25                  30

Thr Ser Val Thr Gly Leu Val Pro Ala Gly Ala Asp Glu Val Ser Ala
            35                  40                  45

Gln Ala Ala Thr Ala Phe Thr Ser Glu Gly Ile Gln Leu Leu Ala Ser
        50                  55                  60

Asn Ala Ser Ala Gln Asp Gln Leu His Arg Ala Gly Glu Ala Val Gln
65                  70                  75                  80

Asp Val Ala Arg Thr Tyr Ser Gln Ile Asp Asp Gly Ala Ala Gly Val
                85                  90                  95

Phe Ala Glu

<210> SEQ ID NO 3
<211> LENGTH: 368
<212> TYPE: PRT
<213> ORGANISM: Mycobacterium tuberculosis

<400> SEQUENCE: 3

Met Leu Trp His Ala Met Pro Pro Glu Leu Asn Thr Ala Arg Leu Met
1               5                   10                  15

Ala Gly Ala Gly Pro Ala Pro Met Leu Ala Ala Ala Gly Trp Gln
                20                  25                  30

Thr Leu Ser Ala Ala Leu Asp Ala Gln Ala Val Glu Leu Thr Ala Arg
            35                  40                  45

Leu Asn Ser Leu Gly Glu Ala Trp Thr Gly Gly Gly Ser Asp Lys Ala
        50                  55                  60
```

-continued

```
Leu Ala Ala Ala Thr Pro Met Val Val Trp Leu Gln Thr Ala Ser Thr
65                  70                  75                  80

Gln Ala Lys Thr Arg Ala Met Gln Ala Thr Ala Gln Ala Ala Ala Tyr
                85                  90                  95

Thr Gln Ala Met Ala Thr Thr Pro Ser Leu Pro Glu Ile Ala Ala Asn
            100                 105                 110

His Ile Thr Gln Ala Val Leu Thr Ala Thr Asn Phe Phe Gly Ile Asn
        115                 120                 125

Thr Ile Pro Ile Ala Leu Thr Glu Met Asp Tyr Phe Ile Arg Met Trp
    130                 135                 140

Asn Gln Ala Ala Leu Ala Met Glu Val Tyr Gln Ala Glu Thr Ala Val
145                 150                 155                 160

Asn Thr Leu Phe Glu Lys Leu Glu Pro Met Ala Ser Ile Leu Asp Pro
                165                 170                 175

Gly Ala Ser Gln Ser Thr Thr Asn Pro Ile Phe Gly Met Pro Ser Pro
            180                 185                 190

Gly Ser Ser Thr Pro Val Gly Gln Leu Pro Pro Ala Ala Thr Gln Thr
        195                 200                 205

Leu Gly Gln Leu Gly Glu Met Ser Gly Pro Met Gln Gln Leu Thr Gln
    210                 215                 220

Pro Leu Gln Gln Val Thr Ser Leu Phe Ser Gln Val Gly Gly Thr Gly
225                 230                 235                 240

Gly Gly Asn Pro Ala Asp Glu Glu Ala Ala Gln Met Gly Leu Leu Gly
                245                 250                 255

Thr Ser Pro Leu Ser Asn His Pro Leu Ala Gly Gly Ser Gly Pro Ser
            260                 265                 270

Ala Gly Ala Gly Leu Leu Arg Ala Glu Ser Leu Pro Gly Ala Gly Gly
        275                 280                 285

Ser Leu Thr Arg Thr Pro Leu Met Ser Gln Leu Ile Glu Lys Pro Val
    290                 295                 300

Ala Pro Ser Val Met Pro Ala Ala Ala Ala Gly Ser Ser Ala Thr Gly
305                 310                 315                 320

Gly Ala Ala Pro Val Gly Ala Gly Ala Met Gly Gln Gly Ala Gln Ser
                325                 330                 335

Gly Gly Ser Thr Arg Pro Gly Leu Val Ala Pro Ala Pro Leu Ala Gln
            340                 345                 350

Glu Arg Glu Glu Asp Asp Glu Asp Asp Trp Asp Glu Glu Asp Asp Trp
        355                 360                 365

<210> SEQ ID NO 4
<211> LENGTH: 100
<212> TYPE: PRT
<213> ORGANISM: Mycobacterium tuberculosis

<400> SEQUENCE: 4

Met Ala Glu Met Lys Thr Asp Ala Ala Thr Leu Ala Gln Glu Ala Gly
 1               5                  10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80
```

```
Val Gln Tyr Ser Arg Ala Asp Glu Glu Gln Gln Ala Leu Ser Ser
             85                  90                  95

Gln Met Gly Phe
            100

<210> SEQ ID NO 5
<211> LENGTH: 666
<212> TYPE: PRT
<213> ORGANISM: Mycobacterium tuberculosis

<400> SEQUENCE: 5

Met Ala Ala Asp Tyr Asp Lys Leu Phe Arg Pro His Glu Gly Met Glu
 1               5                  10                  15

Ala Pro Asp Asp Met Ala Ala Gln Pro Phe Phe Asp Pro Ser Ala Ser
             20                  25                  30

Phe Pro Pro Ala Pro Ala Ser Ala Asn Leu Pro Lys Pro Asn Gly Gln
         35                  40                  45

Thr Pro Pro Pro Thr Ser Asp Asp Leu Ser Glu Arg Phe Val Ser Ala
     50                  55                  60

Pro Pro Pro Pro Pro Pro Pro Pro Pro Pro Pro Thr Pro Met
65                  70                  75                  80

Pro Ile Ala Ala Gly Glu Pro Pro Ser Pro Glu Pro Ala Ala Ser Lys
                 85                  90                  95

Pro Pro Thr Pro Pro Met Pro Ile Ala Gly Pro Glu Pro Ala Pro Pro
            100                 105                 110

Lys Pro Pro Thr Pro Pro Met Pro Ile Ala Gly Pro Glu Pro Ala Pro
        115                 120                 125

Pro Lys Pro Pro Thr Pro Pro Met Pro Ile Ala Gly Pro Ala Pro Thr
    130                 135                 140

Pro Thr Glu Ser Gln Leu Ala Pro Pro Arg Pro Pro Thr Pro Gln Thr
145                 150                 155                 160

Pro Thr Gly Ala Pro Gln Gln Pro Glu Ser Pro Ala Pro His Val Pro
                165                 170                 175

Ser His Gly Pro His Gln Pro Arg Arg Thr Ala Pro Ala Pro Pro Trp
            180                 185                 190

Ala Lys Met Pro Ile Gly Glu Pro Pro Ala Pro Ser Arg Pro Ser
        195                 200                 205

Ala Ser Pro Ala Glu Pro Pro Thr Arg Pro Ala Pro Gln His Ser Arg
    210                 215                 220

Arg Ala Arg Arg Gly His Arg Tyr Arg Thr Asp Thr Glu Arg Asn Val
225                 230                 235                 240

Gly Lys Val Ala Thr Gly Pro Ser Ile Gln Ala Arg Leu Arg Ala Glu
                245                 250                 255

Glu Ala Ser Gly Ala Gln Leu Ala Pro Gly Thr Glu Pro Ser Pro Ala
            260                 265                 270

Pro Leu Gly Gln Pro Arg Ser Tyr Leu Ala Pro Pro Thr Arg Pro Ala
        275                 280                 285

Pro Thr Glu Pro Pro Pro Ser Pro Ser Pro Gln Arg Asn Ser Gly Arg
    290                 295                 300

Arg Ala Glu Arg Arg Val His Pro Asp Leu Ala Gln His Ala Ala
305                 310                 315                 320

Ala Gln Pro Asp Ser Ile Thr Ala Ala Thr Thr Gly Gly Arg Arg
                325                 330                 335

Lys Arg Ala Ala Pro Asp Leu Asp Ala Thr Gln Lys Ser Leu Arg Pro
```

```
                340             345             350
Ala Ala Lys Gly Pro Lys Val Lys Val Lys Pro Gln Lys Pro Lys
            355             360             365

Ala Thr Lys Pro Pro Lys Val Val Ser Gln Arg Gly Trp Arg His Trp
        370             375             380

Val His Ala Leu Thr Arg Ile Asn Leu Gly Leu Ser Pro Asp Glu Lys
385             390             395             400

Tyr Glu Leu Asp Leu His Ala Arg Val Arg Arg Asn Pro Arg Gly Ser
            405             410             415

Tyr Gln Ile Ala Val Val Gly Leu Lys Gly Ala Gly Lys Thr Thr
            420             425             430

Leu Thr Ala Ala Leu Gly Ser Thr Leu Ala Gln Val Arg Ala Asp Arg
            435             440             445

Ile Leu Ala Leu Asp Ala Asp Pro Gly Ala Gly Asn Leu Ala Asp Arg
            450             455             460

Val Gly Arg Gln Ser Gly Ala Thr Ile Ala Asp Val Leu Ala Glu Lys
465             470             475             480

Glu Leu Ser His Tyr Asn Asp Ile Arg Ala His Thr Ser Val Asn Ala
            485             490             495

Val Asn Leu Glu Val Leu Pro Ala Pro Glu Tyr Ser Ser Ala Gln Arg
            500             505             510

Ala Leu Ser Asp Ala Asp Trp His Phe Ile Ala Asp Pro Ala Ser Arg
            515             520             525

Phe Tyr Asn Leu Val Leu Ala Asp Cys Gly Ala Gly Phe Phe Asp Pro
            530             535             540

Leu Thr Arg Gly Val Leu Ser Thr Val Ser Gly Val Val Val Ala
545             550             555             560

Ser Val Ser Ile Asp Gly Ala Gln Gln Ala Ser Val Ala Leu Asp Trp
            565             570             575

Leu Arg Asn Asn Gly Tyr Gln Asp Leu Ala Ser Arg Ala Cys Val Val
            580             585             590

Ile Asn His Ile Met Pro Gly Glu Pro Asn Val Ala Val Lys Asp Leu
            595             600             605

Val Arg His Phe Glu Gln Gln Val Gln Pro Gly Arg Val Val Val Met
            610             615             620

Pro Trp Asp Arg His Ile Ala Ala Gly Thr Glu Ile Ser Leu Asp Leu
625             630             635             640

Leu Asp Pro Ile Tyr Lys Arg Lys Val Leu Glu Leu Ala Ala Ala Leu
            645             650             655

Ser Asp Asp Phe Glu Arg Ala Gly Arg Arg
            660             665

<210> SEQ ID NO 6
<211> LENGTH: 511
<212> TYPE: PRT
<213> ORGANISM: Mycobacterium tuberculosis

<400> SEQUENCE: 6

Leu Ser Ala Pro Ala Val Ala Ala Gly Pro Thr Ala Ala Gly Ala Thr
1               5                   10                  15

Ala Ala Arg Pro Ala Thr Thr Arg Val Thr Ile Leu Thr Gly Arg Arg
            20                  25                  30

Met Thr Asp Leu Val Leu Pro Ala Ala Val Pro Met Glu Thr Tyr Ile
            35                  40                  45
```

-continued

```
Asp Asp Thr Val Ala Val Leu Ser Glu Val Leu Glu Asp Thr Pro Ala
 50                  55                  60

Asp Val Leu Gly Gly Phe Asp Phe Thr Ala Gln Gly Val Trp Ala Phe
 65                  70                  75                  80

Ala Arg Pro Gly Ser Pro Pro Leu Lys Leu Asp Gln Ser Leu Asp Asp
                 85                  90                  95

Ala Gly Val Val Asp Gly Ser Leu Leu Thr Leu Val Ser Val Ser Arg
                100                 105                 110

Thr Glu Arg Tyr Arg Pro Leu Val Glu Asp Val Ile Asp Ala Ile Ala
            115                 120                 125

Val Leu Asp Glu Ser Pro Glu Phe Asp Arg Thr Ala Leu Asn Arg Phe
130                 135                 140

Val Gly Ala Ala Ile Pro Leu Leu Thr Ala Pro Val Ile Gly Met Ala
145                 150                 155                 160

Met Arg Ala Trp Trp Glu Thr Gly Arg Ser Leu Trp Trp Pro Leu Ala
                165                 170                 175

Ile Gly Ile Leu Gly Ile Ala Val Leu Val Gly Ser Phe Val Ala Asn
            180                 185                 190

Arg Phe Tyr Gln Ser Gly His Leu Ala Glu Cys Leu Leu Val Thr Thr
        195                 200                 205

Tyr Leu Leu Ile Ala Thr Ala Ala Leu Ala Val Pro Leu Pro Arg
210                 215                 220

Gly Val Asn Ser Leu Gly Ala Pro Gln Val Ala Gly Ala Ala Thr Ala
225                 230                 235                 240

Val Leu Phe Leu Thr Leu Met Thr Arg Gly Gly Pro Arg Lys Arg His
                245                 250                 255

Glu Leu Ala Ser Phe Ala Val Ile Thr Ala Ile Ala Val Ile Ala Ala
            260                 265                 270

Ala Ala Ala Phe Gly Tyr Gly Tyr Gln Asp Trp Val Pro Ala Gly Gly
        275                 280                 285

Ile Ala Phe Gly Leu Phe Ile Val Thr Asn Ala Ala Lys Leu Thr Val
290                 295                 300

Ala Val Ala Arg Ile Ala Leu Pro Pro Ile Pro Val Pro Gly Glu Thr
305                 310                 315                 320

Val Asp Asn Glu Glu Leu Leu Asp Pro Val Ala Thr Pro Glu Ala Thr
                325                 330                 335

Ser Glu Glu Thr Pro Thr Trp Gln Ala Ile Ile Ala Ser Val Pro Ala
            340                 345                 350

Ser Ala Val Arg Leu Thr Glu Arg Ser Lys Leu Ala Lys Gln Leu Leu
        355                 360                 365

Ile Gly Tyr Val Thr Ser Gly Thr Leu Ile Leu Ala Ala Gly Ala Ile
370                 375                 380

Ala Val Val Val Arg Gly His Phe Phe Val His Ser Leu Val Val Ala
385                 390                 395                 400

Gly Leu Ile Thr Thr Val Cys Gly Phe Arg Ser Arg Leu Tyr Ala Glu
                405                 410                 415

Arg Trp Cys Ala Trp Ala Leu Leu Ala Ala Thr Val Ala Ile Pro Thr
            420                 425                 430

Gly Leu Thr Ala Lys Leu Ile Ile Trp Tyr Pro His Tyr Ala Trp Leu
        435                 440                 445

Leu Leu Ser Val Tyr Leu Thr Val Ala Leu Val Ala Leu Val Val Val
450                 455                 460

Gly Ser Met Ala His Val Arg Arg Val Ser Pro Val Val Lys Arg Thr
```

```
                    465                 470                 475                 480
Leu Glu Leu Ile Asp Gly Ala Met Ile Ala Ala Ile Ile Pro Met Leu
                485                 490                 495

Leu Trp Ile Thr Gly Val Tyr Asp Thr Val Arg Asn Ile Arg Phe
            500                 505                 510

<210> SEQ ID NO 7
<211> LENGTH: 280
<212> TYPE: PRT
<213> ORGANISM: Mycobacterium tuberculosis

<400> SEQUENCE: 7

Met Ala Glu Pro Leu Ala Val Asp Pro Thr Gly Leu Ser Ala Ala
  1               5                  10                  15

Ala Lys Leu Ala Gly Leu Val Phe Pro Gln Pro Pro Ala Pro Ile Ala
                 20                  25                  30

Val Ser Gly Thr Asp Ser Val Ala Ala Ile Asn Glu Thr Met Pro
             35                  40                  45

Ser Ile Glu Ser Leu Val Ser Asp Gly Leu Pro Gly Val Lys Ala Ala
         50                  55                  60

Leu Thr Arg Thr Ala Ser Asn Met Asn Ala Ala Ala Asp Val Tyr Ala
 65                  70                  75                  80

Lys Thr Asp Gln Ser Leu Gly Thr Ser Leu Ser Gln Tyr Ala Phe Gly
                 85                  90                  95

Ser Ser Gly Glu Gly Leu Ala Gly Val Ala Ser Val Gly Gly Gln Pro
            100                 105                 110

Ser Gln Ala Thr Gln Leu Leu Ser Thr Pro Val Ser Gln Val Thr Thr
            115                 120                 125

Gln Leu Gly Glu Thr Ala Ala Glu Leu Ala Pro Arg Val Val Ala Thr
        130                 135                 140

Val Pro Gln Leu Val Gln Leu Ala Pro His Ala Val Gln Met Ser Gln
145                 150                 155                 160

Asn Ala Ser Pro Ile Ala Gln Thr Ile Ser Gln Thr Ala Gln Gln Ala
                165                 170                 175

Ala Gln Ser Ala Gln Gly Gly Ser Gly Pro Met Pro Ala Gln Leu Ala
            180                 185                 190

Ser Ala Glu Lys Pro Ala Thr Glu Gln Ala Glu Pro Val His Glu Val
            195                 200                 205

Thr Asn Asp Asp Gln Gly Asp Gln Asp Val Gln Pro Ala Glu Val
        210                 215                 220

Val Ala Ala Arg Asp Glu Ala Gly Ala Ser Pro Gly Gln Gln
225                 230                 235                 240

Pro Gly Gly Gly Val Pro Ala Gln Ala Met Asp Thr Gly Ala Gly Ala
                245                 250                 255

Arg Pro Ala Ala Ser Pro Leu Ala Ala Pro Val Asp Pro Ser Thr Pro
            260                 265                 270

Ala Pro Ser Thr Thr Thr Leu
            275                 280

<210> SEQ ID NO 8
<211> LENGTH: 729
<212> TYPE: PRT
<213> ORGANISM: Mycobacterium tuberculosis

<400> SEQUENCE: 8

Met Ser Ile Thr Arg Pro Thr Gly Ser Tyr Ala Arg Gln Met Leu Asp
```

```
  1               5                   10                  15
Pro Gly Gly Trp Val Glu Ala Asp Glu Asp Thr Phe Tyr Asp Arg Ala
                 20                  25                  30

Gln Glu Tyr Ser Gln Val Leu Gln Arg Val Thr Asp Val Leu Asp Thr
                 35                  40                  45

Cys Arg Gln Gln Lys Gly His Val Phe Glu Gly Leu Trp Ser Gly
    50                  55                  60

Gly Ala Asn Ala Ala Asn Gly Ala Leu Gly Ala Asn Ile Asn Gln
65                  70                  75                  80

Leu Met Thr Leu Gln Asp Tyr Leu Ala Thr Val Ile Thr Trp His Arg
                 85                  90                  95

His Ile Ala Gly Leu Ile Glu Gln Ala Lys Ser Asp Ile Gly Asn Asn
                 100                 105                 110

Val Asp Gly Ala Gln Arg Glu Ile Asp Ile Leu Glu Asn Asp Pro Ser
                 115                 120                 125

Leu Asp Ala Asp Glu Arg His Thr Ala Ile Asn Ser Leu Val Thr Ala
130                 135                 140

Thr His Gly Ala Asn Val Ser Leu Val Ala Glu Thr Ala Glu Arg Val
145                 150                 155                 160

Leu Glu Ser Lys Asn Trp Lys Pro Pro Lys Asn Ala Leu Glu Asp Leu
                 165                 170                 175

Leu Gln Gln Lys Ser Pro Pro Pro Asp Val Pro Thr Leu Val Val
                 180                 185                 190

Pro Ser Pro Gly Thr Pro Gly Thr Pro Gly Thr Pro Ile Thr Pro Gly
                 195                 200                 205

Thr Pro Ile Thr Pro Gly Thr Pro Ile Thr Pro Ile Pro Gly Ala Pro
210                 215                 220

Val Thr Pro Ile Thr Pro Thr Pro Gly Thr Pro Val Thr Pro Val Thr
225                 230                 235                 240

Pro Gly Lys Pro Val Thr Pro Val Thr Pro Val Lys Pro Gly Thr Pro
                 245                 250                 255

Gly Glu Pro Thr Pro Ile Thr Pro Val Thr Pro Val Ala Pro Ala
                 260                 265                 270

Thr Pro Ala Thr Pro Ala Thr Pro Val Thr Pro Ala Pro Ala Pro His
                 275                 280                 285

Pro Gln Pro Ala Pro Ala Pro Ser Pro Gly Pro Gln Pro Val
                 290                 295                 300

Thr Pro Ala Thr Pro Gly Pro Ser Gly Pro Ala Thr Pro Gly Thr Pro
305                 310                 315                 320

Gly Gly Glu Pro Ala Pro His Val Lys Pro Ala Ala Leu Ala Glu Gln
                 325                 330                 335

Pro Gly Val Pro Gly Gln His Ala Gly Gly Thr Gln Ser Gly Pro
                 340                 345                 350

Ala His Ala Asp Glu Ser Ala Ala Ser Val Thr Pro Ala Ala Ser
                 355                 360                 365

Gly Val Pro Gly Ala Arg Ala Ala Ala Pro Ser Gly Thr Ala
                 370                 375                 380

Val Gly Ala Gly Ala Arg Ser Val Gly Thr Ala Ala Ser Gly
385                 390                 395                 400

Ala Gly Ser His Ala Thr Gly Arg Ala Pro Val Ala Thr Ser Asp
                 405                 410                 415

Lys Ala Ala Pro Ser Thr Arg Ala Ser Ala Arg Thr Ala Pro
                 420                 425                 430
```

```
       Pro Ala Arg Pro Pro Ser Thr Asp His Ile Asp Lys Pro Asp Arg Ser
               435                 440                 445

Glu Ser Ala Asp Asp Gly Thr Pro Val Ser Met Ile Pro Val Ser Ala
       450                 455                 460

Ala Arg Ala Ala Arg Asp Ala Ala Thr Ala Ala Ala Ser Ala Arg Gln
       465                 470                 475                 480

Arg Gly Arg Gly Asp Ala Leu Arg Leu Ala Arg Ile Ala Ala Ala
                       485                 490                 495

Leu Asn Ala Ser Asp Asn Ala Gly Asp Tyr Gly Phe Phe Trp Ile
                   500                 505                 510

Thr Ala Val Thr Thr Asp Gly Ser Ile Val Val Ala Asn Ser Tyr Gly
                       515                 520                 525

Leu Ala Tyr Ile Pro Asp Gly Met Glu Leu Pro Asn Lys Val Tyr Leu
                   530                 535                 540

Ala Ser Ala Asp His Ala Ile Pro Val Asp Glu Ile Ala Arg Cys Ala
       545                 550                 555                 560

Thr Tyr Pro Val Leu Ala Val Gln Ala Trp Ala Ala Phe His Asp Met
                       565                 570                 575

Thr Leu Arg Ala Val Ile Gly Thr Ala Glu Gln Leu Ala Ser Ser Asp
                   580                 585                 590

Pro Gly Val Ala Lys Ile Val Leu Glu Pro Asp Asp Ile Pro Glu Ser
                       595                 600                 605

Gly Lys Met Thr Gly Arg Ser Arg Leu Glu Val Val Asp Pro Ser Ala
                   610                 615                 620

Ala Ala Gln Leu Ala Asp Thr Thr Asp Gln Arg Leu Leu Asp Leu Leu
       625                 630                 635                 640

Pro Pro Ala Pro Val Asp Val Asn Pro Pro Gly Asp Glu Arg His Met
                       645                 650                 655

Leu Trp Phe Glu Leu Met Lys Pro Met Thr Ser Thr Ala Thr Gly Arg
                   660                 665                 670

Glu Ala Ala His Leu Arg Ala Phe Arg Ala Tyr Ala Ala His Ser Gln
                   675                 680                 685

Glu Ile Ala Leu His Gln Ala His Thr Ala Thr Asp Ala Ala Val Gln
                   690                 695                 700

Arg Val Ala Val Ala Asp Trp Leu Tyr Trp Gln Tyr Val Thr Gly Leu
       705                 710                 715                 720

Leu Asp Arg Ala Leu Ala Ala Ala Cys
                       725

<210> SEQ ID NO 9
<211> LENGTH: 1776
<212> TYPE: DNA
<213> ORGANISM: Mycobacterium tuberculosis
<220> FEATURE:
<221> NAME/KEY: CDS
<222> LOCATION: (1)...(1773)

<400> SEQUENCE: 9 atg act gct gaa ccg gaa gta cgg acg ctg cgc gag gtt gtg ctg gac    48
Met Thr Ala Glu Pro Glu Val Arg Thr Leu Arg Glu Val Val Leu Asp
 1               5                  10                  15 cag ctc ggc act gct gaa tcg cgt gcg tac aag atg tgg ctg ccg ccg    96
Gln Leu Gly Thr Ala Glu Ser Arg Ala Tyr Lys Met Trp Leu Pro Pro
             20                  25                  30 ttg acc aat ccg gtc ccg ctc aac gag ctc atc gcc cgt gat cgg cga   144
Leu Thr Asn Pro Val Pro Leu Asn Glu Leu Ile Ala Arg Asp Arg Arg
```

```
               35                  40                  45
caa ccc ctg cga ttt gcc ctg ggg atc atg gat gaa ccg cgc cgc cat    192
Gln Pro Leu Arg Phe Ala Leu Gly Ile Met Asp Glu Pro Arg Arg His
 50                  55                  60 cta cag gat gtg tgg ggc gta gac gtt tcc ggg gcc ggc ggc aac atc    240
Leu Gln Asp Val Trp Gly Val Asp Val Ser Gly Ala Gly Gly Asn Ile
 65                  70                  75                  80 ggt att ggg ggc gca cct caa acc ggg aag tcg acg cta ctg cag acg    288
Gly Ile Gly Gly Ala Pro Gln Thr Gly Lys Ser Thr Leu Leu Gln Thr
                 85                  90                  95 atg gtg atg tcg gcc gcc gcc aca cac tca ccg cgc aac gtt cag ttc    336
Met Val Met Ser Ala Ala Ala Thr His Ser Pro Arg Asn Val Gln Phe
            100                 105                 110 tat tgc atc gac cta ggt ggc ggc ggg ctg atc tat ctc gaa aac ctt    384
Tyr Cys Ile Asp Leu Gly Gly Gly Gly Leu Ile Tyr Leu Glu Asn Leu
        115                 120                 125 cca cac gtc ggt ggg gta gcc aat cgg tcc gag ccc gac aag gtc aac    432
Pro His Val Gly Gly Val Ala Asn Arg Ser Glu Pro Asp Lys Val Asn
    130                 135                 140 cgg gtg gtc gca gag atg caa gcc gtc atg cgg caa cgg gaa acc acc    480
Arg Val Val Ala Glu Met Gln Ala Val Met Arg Gln Arg Glu Thr Thr
145                 150                 155                 160 ttc aag gaa cac cga gtg ggc tcg atc ggg atg tac cgg cag ctg cgt    528
Phe Lys Glu His Arg Val Gly Ser Ile Gly Met Tyr Arg Gln Leu Arg
                165                 170                 175 gac gat cca agt caa ccc gtt gcg tcc gat cca tac ggc gac gtc ttt    576
Asp Asp Pro Ser Gln Pro Val Ala Ser Asp Pro Tyr Gly Asp Val Phe
            180                 185                 190 ctg atc atc gac gga tgg ccc ggt ttt gtc ggc gag ttc ccc gac ctt    624
Leu Ile Ile Asp Gly Trp Pro Gly Phe Val Gly Glu Phe Pro Asp Leu
        195                 200                 205 gag ggg cag gtt caa gat ctg gcc gcc cag ggg ctg gcg ttc ggc gtc    672
Glu Gly Gln Val Gln Asp Leu Ala Ala Gln Gly Leu Ala Phe Gly Val
    210                 215                 220 cac gtc atc atc tcc acg cca cgc tgg aca gag ctg aag tcg cgt gtt    720
His Val Ile Ile Ser Thr Pro Arg Trp Thr Glu Leu Lys Ser Arg Val
225                 230                 235                 240 cgc gac tac ctc ggc acc aag atc gag ttc cgg ctt ggt gac gtc aat    768
Arg Asp Tyr Leu Gly Thr Lys Ile Glu Phe Arg Leu Gly Asp Val Asn
                245                 250                 255 gaa acc cag atc gac cgg att acc cgc gag atc ccg gcg aat cgt ccg    816
Glu Thr Gln Ile Asp Arg Ile Thr Arg Glu Ile Pro Ala Asn Arg Pro
            260                 265                 270 ggt cgg gca gtg tcg atg gaa aag cac cat ctg atg atc ggc gtg ccc    864
Gly Arg Ala Val Ser Met Glu Lys His His Leu Met Ile Gly Val Pro
        275                 280                 285 agg ttc gac ggc gtg cac agc gcc gat aac ctg gtg gag gcg atc acc    912
Arg Phe Asp Gly Val His Ser Ala Asp Asn Leu Val Glu Ala Ile Thr
    290                 295                 300 gcg ggg gtg acg cag atc gct tcc cag cac acc gaa cag gca cct ccg    960
Ala Gly Val Thr Gln Ile Ala Ser Gln His Thr Glu Gln Ala Pro Pro
305                 310                 315                 320 gtg cgg gtc ctg ccg gag cgt atc cac ctg cac gaa ctc gac ccg aac   1008
Val Arg Val Leu Pro Glu Arg Ile His Leu His Glu Leu Asp Pro Asn
                325                 330                 335 ccg ccg gga cca gag tcc gac tac cgc act cgc tgg gag att ccg atc   1056
Pro Pro Gly Pro Glu Ser Asp Tyr Arg Thr Arg Trp Glu Ile Pro Ile
            340                 345                 350 ggc ttg cgc gag acg gac ctg acg ccg gct cac tgc cac atg cac acg   1104
```

```
                Gly Leu Arg Glu Thr Asp Leu Thr Pro Ala His Cys His Met His Thr
                            355                 360                 365 aac ccg cac cta ctg atc ttc ggt gcg gcc aaa tcg ggc aag acg acc              1152
Asn Pro His Leu Leu Ile Phe Gly Ala Ala Lys Ser Gly Lys Thr Thr
        370                 375                 380 att gcc cac gcg atc gcg cgc gcc att tgt gcc cga aac agt ccc cag              1200
Ile Ala His Ala Ile Ala Arg Ala Ile Cys Ala Arg Asn Ser Pro Gln
385                 390                 395                 400 cag gtg cgg ttc atg ctc gcg gac tac cgc tcg ggc ctg ctg gac gcg              1248
Gln Val Arg Phe Met Leu Ala Asp Tyr Arg Ser Gly Leu Leu Asp Ala
                405                 410                 415 gtg ccg gac acc cat ctg ctg ggc gcc ggc gcg atc aac cgc aac agc              1296
Val Pro Asp Thr His Leu Leu Gly Ala Gly Ala Ile Asn Arg Asn Ser
            420                 425                 430 gcg tcg cta gac gag gcc gtt caa gca ctg gcg gtc aac ctg aag aag              1344
Ala Ser Leu Asp Glu Ala Val Gln Ala Leu Ala Val Asn Leu Lys Lys
        435                 440                 445 cgg ttg ccg ccg acc gac ctg acg acg gcg cag cta cgc tcg cgt tcg              1392
Arg Leu Pro Pro Thr Asp Leu Thr Thr Ala Gln Leu Arg Ser Arg Ser
450                 455                 460 tgg tgg agc gga ttt gac gtc gtg ctt ctg gtc gac gat tgg cac atg              1440
Trp Trp Ser Gly Phe Asp Val Val Leu Leu Val Asp Asp Trp His Met
465                 470                 475                 480 atc gtg ggt gcc gcc ggg ggg atg ccg ccg atg gca ccg ctg gcc ccg              1488
Ile Val Gly Ala Ala Gly Gly Met Pro Pro Met Ala Pro Leu Ala Pro
                485                 490                 495 tta ttg ccg gcg gcg gca gat atc ggg ttg cac atc att gtc acc tgt              1536
Leu Leu Pro Ala Ala Ala Asp Ile Gly Leu His Ile Ile Val Thr Cys
            500                 505                 510 cag atg agc cag gct tac aag gca acc atg gac aag ttc gtc ggc gcc              1584
Gln Met Ser Gln Ala Tyr Lys Ala Thr Met Asp Lys Phe Val Gly Ala
        515                 520                 525 gca ttc ggg tcg ggc gct ccg aca atg ttc ctt tcg ggc gag aag cag              1632
Ala Phe Gly Ser Gly Ala Pro Thr Met Phe Leu Ser Gly Glu Lys Gln
    530                 535                 540 gaa ttc cca tcc agt gag ttc aag gtc aag cgg cgc cct cct ggc cag              1680
Glu Phe Pro Ser Ser Glu Phe Lys Val Lys Arg Arg Pro Pro Gly Gln
545                 550                 555                 560 gca ttt ctc gtc tcg cca gac ggc aaa gag gtc atc cag gcc ccc tac              1728
Ala Phe Leu Val Ser Pro Asp Gly Lys Glu Val Ile Gln Ala Pro Tyr
                565                 570                 575 atc gag cct cca gaa gaa gtg ttc gca gca ccc cca agc gcc ggt                  1773
Ile Glu Pro Pro Glu Glu Val Phe Ala Ala Pro Pro Ser Ala Gly
            580                 585                 590 taa                                                                          1776

<210> SEQ ID NO 10
<211> LENGTH: 300
<212> TYPE: DNA
<213> ORGANISM: Mycobacterium tuberculosis
<220> FEATURE:
<221> NAME/KEY: CDS
<222> LOCATION: (1)...(297)

<400> SEQUENCE: 10 atg gaa aaa atg tca cat gat ccg atc gct gcc gac att ggc acg caa              48
Met Glu Lys Met Ser His Asp Pro Ile Ala Ala Asp Ile Gly Thr Gln
1               5                   10                  15 gtg agc gac aac gct ctg cac ggc gtg acg gcc ggc tcg acg gcg ctg              96
Val Ser Asp Asn Ala Leu His Gly Val Thr Ala Gly Ser Thr Ala Leu
            20                  25                  30
```

```
acg tcg gtg acc ggg ctg gtt ccc gcg ggg gcc gat gag gtc tcc gcc      144
Thr Ser Val Thr Gly Leu Val Pro Ala Gly Ala Asp Glu Val Ser Ala
            35                  40                  45 caa gcg gcg acg gcg ttc aca tcg gag ggc atc caa ttg ctg gct tcc      192
Gln Ala Ala Thr Ala Phe Thr Ser Glu Gly Ile Gln Leu Leu Ala Ser
 50                  55                  60 aat gca tcg gcc caa gac cag ctc cac cgt gcg ggc gaa gcg gtc cag      240
Asn Ala Ser Ala Gln Asp Gln Leu His Arg Ala Gly Glu Ala Val Gln
 65                  70                  75                  80 gac gtc gcc cgc acc tat tcg caa atc gac gac ggc gcc gcc ggc gtc      288
Asp Val Ala Arg Thr Tyr Ser Gln Ile Asp Asp Gly Ala Ala Gly Val
                85                  90                  95 ttc gcc gaa tag                                                      300
Phe Ala Glu <210> SEQ ID NO 11
<211> LENGTH: 1107
<212> TYPE: DNA
<213> ORGANISM: Mycobacterium tuberculosis
<220> FEATURE:
<221> NAME/KEY: CDS
<222> LOCATION: (1)...(1104)

<400> SEQUENCE: 11 atg ctg tgg cac gca atg cca ccg gag cta aat acc gca cgg ctg atg       48
Met Leu Trp His Ala Met Pro Pro Glu Leu Asn Thr Ala Arg Leu Met
 1               5                  10                  15 gcc ggc gcg ggt ccg gct cca atg ctt gcg gcg gcc gcg gga tgg cag       96
Ala Gly Ala Gly Pro Ala Pro Met Leu Ala Ala Ala Ala Gly Trp Gln
                20                  25                  30 acg ctt tcg gcg gct ctg gac gct cag gcc gtc gag ttg acc gcg cgc      144
Thr Leu Ser Ala Ala Leu Asp Ala Gln Ala Val Glu Leu Thr Ala Arg
            35                  40                  45 ctg aac tct ctg gga gaa gcc tgg act gga ggt ggc agc gac aag gcg      192
Leu Asn Ser Leu Gly Glu Ala Trp Thr Gly Gly Gly Ser Asp Lys Ala
 50                  55                  60 ctt gcg gct gca acg ccg atg gtg gtc tgg cta caa acc gca tca aca      240
Leu Ala Ala Ala Thr Pro Met Val Val Trp Leu Gln Thr Ala Ser Thr
 65                  70                  75                  80 cag gcc aag acc cgt gcg atg cag gcg acg gcg caa gcc gcg gca tac      288
Gln Ala Lys Thr Arg Ala Met Gln Ala Thr Ala Gln Ala Ala Ala Tyr
                85                  90                  95 acc cag gcc atg gcc acg acg ccg tcg ctg ccg gag atc gcc gcc aac      336
Thr Gln Ala Met Ala Thr Thr Pro Ser Leu Pro Glu Ile Ala Ala Asn
                100                 105                 110 cac atc acc cag gcc gtc ctt acg gcc acc aac ttc ttc ggt atc aac      384
His Ile Thr Gln Ala Val Leu Thr Ala Thr Asn Phe Phe Gly Ile Asn
            115                 120                 125 acg atc ccg atc gcg ttg acc gag atg gat tat ttc atc cgt atg tgg      432
Thr Ile Pro Ile Ala Leu Thr Glu Met Asp Tyr Phe Ile Arg Met Trp
130                 135                 140 aac cag gca gcc ctg gca atg gag gtc tac cag gcc gag acc gcg gtt      480
Asn Gln Ala Ala Leu Ala Met Glu Val Tyr Gln Ala Glu Thr Ala Val
145                 150                 155                 160 aac acg ctt ttc gag aag ctc gag ccg atg gcg tcg atc ctt gat ccc      528
Asn Thr Leu Phe Glu Lys Leu Glu Pro Met Ala Ser Ile Leu Asp Pro
                165                 170                 175 ggc gcg agc cag agc acg acg aac ccg atc ttc gga atg ccc tcc cct      576
Gly Ala Ser Gln Ser Thr Thr Asn Pro Ile Phe Gly Met Pro Ser Pro
                180                 185                 190
```

| | | |
|---|---|---|
| ggc agc tca aca ccg gtt ggc cag ttg ccg ccg gcg gct acc cag acc<br>Gly Ser Ser Thr Pro Val Gly Gln Leu Pro Pro Ala Ala Thr Gln Thr<br>195                               200                          205 | | 624 |
| ctc ggc caa ctg ggt gag atg agc ggc ccg atg cag cag ctg acc cag<br>Leu Gly Gln Leu Gly Glu Met Ser Gly Pro Met Gln Gln Leu Thr Gln<br>210                         215                          220 | | 672 |
| ccg ctg cag cag gtg acg tcg ttg ttc agc cag gtg ggc ggc acc ggc<br>Pro Leu Gln Gln Val Thr Ser Leu Phe Ser Gln Val Gly Gly Thr Gly<br>225                               230                          235                       240 | | 720 |
| ggc ggc aac cca gcc gac gag gaa gcc gcg cag atg ggc ctc ctc ggc<br>Gly Gly Asn Pro Ala Asp Glu Glu Ala Ala Gln Met Gly Leu Leu Gly<br>                        245                               250                            255 | | 768 |
| acc agt ccg ctg tcg aac cat ccg ctg gct ggt gga tca ggc ccc agc<br>Thr Ser Pro Leu Ser Asn His Pro Leu Ala Gly Gly Ser Gly Pro Ser<br>                        260                             265                             270 | | 816 |
| gcg ggc gcg ggc ctg ctc cgc gcg gag tcg cta cct ggc gca ggt ggg<br>Ala Gly Ala Gly Leu Leu Arg Ala Glu Ser Leu Pro Gly Ala Gly Gly<br>               275                               280                             285 | | 864 |
| tcg ttg acc cgc acg ccg ctg atg tct cag ctg atc gaa aag ccg gtt<br>Ser Leu Thr Arg Thr Pro Leu Met Ser Gln Leu Ile Glu Lys Pro Val<br>290                               295                          300 | | 912 |
| gcc ccc tcg gtg atg ccg gcg gct gct gcc gga tcg tcg gcg acg ggt<br>Ala Pro Ser Val Met Pro Ala Ala Ala Ala Gly Ser Ser Ala Thr Gly<br>305                               310                             315                       320 | | 960 |
| ggc gcc gct ccg gtg ggt gcg gga gcg atg ggc cag ggt gcg caa tcc<br>Gly Ala Ala Pro Val Gly Ala Gly Ala Met Gly Gln Gly Ala Gln Ser<br>                        325                             330                          335 | | 1008 |
| ggc ggc tcc acc agg ccg ggt ctg gtc gcg ccg gca ccg ctc gcg cag<br>Gly Gly Ser Thr Arg Pro Gly Leu Val Ala Pro Ala Pro Leu Ala Gln<br>                        340                             345                          350 | | 1056 |
| gag cgt gaa gaa gac gac gag gac gac tgg gac gaa gag gac gac tgg<br>Glu Arg Glu Glu Asp Asp Glu Asp Asp Trp Asp Glu Glu Asp Asp Trp<br>355                               360                          365 | | 1104 |
| tga | | 1107 |

<210> SEQ ID NO 12
<211> LENGTH: 303
<212> TYPE: DNA
<213> ORGANISM: Mycobacterium tuberculosis
<220> FEATURE:
<221> NAME/KEY: CDS
<222> LOCATION: (1)...(300)

<400> SEQUENCE: 12

| | | |
|---|---|---|
| atg gca gag atg aag acc gat gcc gct acc ctc gcg cag gag gca ggt<br>Met Ala Glu Met Lys Thr Asp Ala Ala Thr Leu Ala Gln Glu Ala Gly<br>1                          5                               10                           15 | | 48 |
| aat ttc gag cgg atc tcc ggc gac ctg aaa acc cag atc gac cag gtg<br>Asn Phe Glu Arg Ile Ser Gly Asp Leu Lys Thr Gln Ile Asp Gln Val<br>                  20                           25                           30 | | 96 |
| gag tcg acg gca ggt tcg ttg cag ggc cag tgg cgc ggc gcg gcg ggg<br>Glu Ser Thr Ala Gly Ser Leu Gln Gly Gln Trp Arg Gly Ala Ala Gly<br>               35                             40                            45 | | 144 |
| acg gcc gcc cag gcc gcg gtg gtg cgc ttc caa gaa gca gcc aat aag<br>Thr Ala Ala Gln Ala Ala Val Val Arg Phe Gln Glu Ala Ala Asn Lys<br>50                               55                             60 | | 192 |
| cag aag cag gaa ctc gac gag atc tcg acg aat att cgt cag gcc ggc<br>Gln Lys Gln Glu Leu Asp Glu Ile Ser Thr Asn Ile Arg Gln Ala Gly<br>65                               70                          75                       80 | | 240 |
| gtc caa tac tcg agg gcc gac gag gag cag cag cag gcg ctg tcc tcg<br>Val Gln Tyr Ser Arg Ala Asp Glu Glu Gln Gln Gln Ala Leu Ser Ser | | 288 |

```
                85                   90                   95
caa atg ggc ttc tga                                                           303
Gln Met Gly Phe
        100

<210> SEQ ID NO 13
<211> LENGTH: 2001
<212> TYPE: DNA
<213> ORGANISM: Mycobacterium tuberculosis
<220> FEATURE:
<221> NAME/KEY: CDS
<222> LOCATION: (1)...(1998)

<400> SEQUENCE: 13 atg gcg gcc gac tac gac aag ctc ttc cgg ccg cac gaa ggt atg gaa              48
Met Ala Ala Asp Tyr Asp Lys Leu Phe Arg Pro His Glu Gly Met Glu
 1               5                  10                  15 gct ccg gac gat atg gca gcg cag ccg ttc ttc gac ccc agt gct tcg              96
Ala Pro Asp Asp Met Ala Ala Gln Pro Phe Phe Asp Pro Ser Ala Ser
                20                  25                  30 ttt ccg ccg gcg ccc gca tcg gca aac cta ccg aag ccc aac ggc cag             144
Phe Pro Pro Ala Pro Ala Ser Ala Asn Leu Pro Lys Pro Asn Gly Gln
            35                  40                  45 act ccg ccc ccg acg tcc gac gac ctg tcg gag cgg ttc gtg tcg gcc             192
Thr Pro Pro Pro Thr Ser Asp Asp Leu Ser Glu Arg Phe Val Ser Ala
         50                  55                  60 ccg ccg ccg cca ccc cca ccc cca cct ccg cct ccg cca act ccg atg             240
Pro Pro Pro Pro Pro Pro Pro Pro Pro Pro Pro Pro Thr Pro Met
 65                  70                  75                  80 ccg atc gcc gca gga gag ccg ccc tcg ccg gaa ccg gcc gca tct aaa             288
Pro Ile Ala Ala Gly Glu Pro Pro Ser Pro Glu Pro Ala Ala Ser Lys
                85                  90                  95 cca ccc aca ccc ccc atg ccc atc gcc gga ccc gaa ccg gcc cca ccc             336
Pro Pro Thr Pro Pro Met Pro Ile Ala Gly Pro Glu Pro Ala Pro Pro
           100                 105                 110 aaa cca ccc aca ccc ccc atg ccc atc gcc gga ccc gaa ccg gcc cca             384
Lys Pro Pro Thr Pro Pro Met Pro Ile Ala Gly Pro Glu Pro Ala Pro
       115                 120                 125 ccc aaa cca ccc aca cct ccg atg ccc atc gcc gga cct gca ccc acc             432
Pro Lys Pro Pro Thr Pro Pro Met Pro Ile Ala Gly Pro Ala Pro Thr
130                 135                 140 cca acc gaa tcc cag ttg gcg ccc ccc aga cca ccg aca cca caa acg             480
Pro Thr Glu Ser Gln Leu Ala Pro Pro Arg Pro Pro Thr Pro Gln Thr
145                 150                 155                 160 cca acc gga gcg ccg cag caa ccg gaa tca ccg gcg ccc cac gta ccc             528
Pro Thr Gly Ala Pro Gln Gln Pro Glu Ser Pro Ala Pro His Val Pro
                165                 170                 175 tcg cac ggg cca cat caa ccc cgg cgc acc gca cca gca ccg ccc tgg             576
Ser His Gly Pro His Gln Pro Arg Arg Thr Ala Pro Ala Pro Pro Trp
            180                 185                 190 gca aag atg cca atc ggc gaa ccc ccg ccc gct ccg tcc aga ccg tct             624
Ala Lys Met Pro Ile Gly Glu Pro Pro Ala Pro Ser Arg Pro Ser
        195                 200                 205 gcg tcc ccg gcc gaa cca ccg acc cgg cct gcc ccc caa cac tcc cga             672
Ala Ser Pro Ala Glu Pro Pro Thr Arg Pro Ala Pro Gln His Ser Arg
    210                 215                 220 cgt gcg cgc cgg ggt cac cgc tat cgc aca gac acc gaa cga aac gtc             720
Arg Ala Arg Arg Gly His Arg Tyr Arg Thr Asp Thr Glu Arg Asn Val
225                 230                 235                 240 ggg aag gta gca act ggt cca tcc atc cag gcg cgg ctg cgg gca gag             768
Gly Lys Val Ala Thr Gly Pro Ser Ile Gln Ala Arg Leu Arg Ala Glu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 245 |     |     |     |     | 250 |     |     |     |     | 255 |     |     |      |
| gaa | gca | tcc | ggc | gcg | cag | ctc | gcc | ccc | gga | acg | gag | ccc | tcg | cca | gcg | 816  |
| Glu | Ala | Ser | Gly | Ala | Gln | Leu | Ala | Pro | Gly | Thr | Glu | Pro | Ser | Pro | Ala |      |
|     |     | 260 |     |     |     |     | 265 |     |     |     |     | 270 |     |     |     |      |
| ccg | ttg | ggc | caa | ccg | aga | tcg | tat | ctg | gct | ccg | ccc | acc | cgc | ccc | gcg | 864  |
| Pro | Leu | Gly | Gln | Pro | Arg | Ser | Tyr | Leu | Ala | Pro | Pro | Thr | Arg | Pro | Ala |      |
|     |     | 275 |     |     |     |     | 280 |     |     |     |     | 285 |     |     |     |      |
| ccg | aca | gaa | cct | ccc | ccc | agc | ccc | tcg | ccg | cag | cgc | aac | tcc | ggt | cgg | 912  |
| Pro | Thr | Glu | Pro | Pro | Pro | Ser | Pro | Ser | Pro | Gln | Arg | Asn | Ser | Gly | Arg |      |
|     | 290 |     |     |     |     | 295 |     |     |     |     | 300 |     |     |     |     |      |
| cgt | gcc | gag | cga | cgc | gtc | cac | ccc | gat | tta | gcc | gcc | caa | cat | gcc | gcg | 960  |
| Arg | Ala | Glu | Arg | Arg | Val | His | Pro | Asp | Leu | Ala | Ala | Gln | His | Ala | Ala |      |
| 305 |     |     |     |     | 310 |     |     |     |     | 315 |     |     |     |     | 320 |      |
| gcg | caa | cct | gat | tca | att | acg | gcc | gca | acc | act | ggc | ggt | cgt | cgc | cgc | 1008 |
| Ala | Gln | Pro | Asp | Ser | Ile | Thr | Ala | Ala | Thr | Thr | Gly | Gly | Arg | Arg | Arg |      |
|     |     |     |     | 325 |     |     |     |     | 330 |     |     |     |     | 335 |     |      |
| aag | cgt | gca | gcg | ccg | gat | ctc | gac | gcg | aca | cag | aaa | tcc | tta | agg | ccg | 1056 |
| Lys | Arg | Ala | Ala | Pro | Asp | Leu | Asp | Ala | Thr | Gln | Lys | Ser | Leu | Arg | Pro |      |
|     |     |     | 340 |     |     |     |     | 345 |     |     |     |     | 350 |     |     |      |
| gcg | gcc | aag | ggg | ccg | aag | gtg | aag | aag | gtg | aag | ccc | cag | aaa | ccg | aag | 1104 |
| Ala | Ala | Lys | Gly | Pro | Lys | Val | Lys | Lys | Val | Lys | Pro | Gln | Lys | Pro | Lys |      |
|     |     | 355 |     |     |     |     | 360 |     |     |     |     | 365 |     |     |     |      |
| gcc | acg | aag | ccg | ccc | aaa | gtg | gtg | tcg | cag | cgc | ggc | tgg | cga | cat | tgg | 1152 |
| Ala | Thr | Lys | Pro | Pro | Lys | Val | Val | Ser | Gln | Arg | Gly | Trp | Arg | His | Trp |      |
|     | 370 |     |     |     |     | 375 |     |     |     |     | 380 |     |     |     |     |      |
| gtg | cat | gcg | ttg | acg | cga | atc | aac | ctg | ggc | ctg | tca | ccc | gac | gag | aag | 1200 |
| Val | His | Ala | Leu | Thr | Arg | Ile | Asn | Leu | Gly | Leu | Ser | Pro | Asp | Glu | Lys |      |
| 385 |     |     |     |     | 390 |     |     |     |     | 395 |     |     |     |     | 400 |      |
| tac | gag | ctg | gac | ctg | cac | gct | cga | gtc | cgc | cgc | aat | ccc | cgc | ggg | tcg | 1248 |
| Tyr | Glu | Leu | Asp | Leu | His | Ala | Arg | Val | Arg | Arg | Asn | Pro | Arg | Gly | Ser |      |
|     |     |     |     | 405 |     |     |     |     | 410 |     |     |     |     | 415 |     |      |
| tat | cag | atc | gcc | gtc | gtc | ggt | ctc | aaa | ggt | ggg | gct | ggc | aaa | acc | acg | 1296 |
| Tyr | Gln | Ile | Ala | Val | Val | Gly | Leu | Lys | Gly | Gly | Ala | Gly | Lys | Thr | Thr |      |
|     |     |     | 420 |     |     |     |     | 425 |     |     |     |     | 430 |     |     |      |
| ctg | aca | gca | gcg | ttg | ggg | tcg | acg | ttg | gct | cag | gtg | cgg | gcc | gac | cgg | 1344 |
| Leu | Thr | Ala | Ala | Leu | Gly | Ser | Thr | Leu | Ala | Gln | Val | Arg | Ala | Asp | Arg |      |
|     |     | 435 |     |     |     |     | 440 |     |     |     |     | 445 |     |     |     |      |
| atc | ctg | gct | cta | gac | gcg | gat | cca | ggc | gcc | gga | aac | ctc | gcc | gat | cgg | 1392 |
| Ile | Leu | Ala | Leu | Asp | Ala | Asp | Pro | Gly | Ala | Gly | Asn | Leu | Ala | Asp | Arg |      |
|     | 450 |     |     |     |     | 455 |     |     |     |     | 460 |     |     |     |     |      |
| gta | ggg | cga | caa | tcg | ggc | gcg | acc | atc | gct | gat | gtg | ctt | gca | gaa | aaa | 1440 |
| Val | Gly | Arg | Gln | Ser | Gly | Ala | Thr | Ile | Ala | Asp | Val | Leu | Ala | Glu | Lys |      |
| 465 |     |     |     |     | 470 |     |     |     |     | 475 |     |     |     |     | 480 |      |
| gag | ctg | tcg | cac | tac | aac | gac | atc | cgc | gca | cac | act | agc | gtc | aat | gcg | 1488 |
| Glu | Leu | Ser | His | Tyr | Asn | Asp | Ile | Arg | Ala | His | Thr | Ser | Val | Asn | Ala |      |
|     |     |     |     | 485 |     |     |     |     | 490 |     |     |     |     | 495 |     |      |
| gtc | aat | ctg | gaa | gtg | ctg | ccg | gca | ccg | gaa | tac | agc | tcg | gcg | cag | cgc | 1536 |
| Val | Asn | Leu | Glu | Val | Leu | Pro | Ala | Pro | Glu | Tyr | Ser | Ser | Ala | Gln | Arg |      |
|     |     |     | 500 |     |     |     |     | 505 |     |     |     |     | 510 |     |     |      |
| gcg | ctc | agc | gac | gcc | gac | tgg | cat | ttc | atc | gcc | gat | cct | gcg | tcg | agg | 1584 |
| Ala | Leu | Ser | Asp | Ala | Asp | Trp | His | Phe | Ile | Ala | Asp | Pro | Ala | Ser | Arg |      |
|     |     | 515 |     |     |     |     | 520 |     |     |     |     | 525 |     |     |     |      |
| ttt | tac | aac | ctc | gtc | ttg | gct | gat | tgt | ggg | gcc | ggc | ttc | ttc | gac | ccg | 1632 |
| Phe | Tyr | Asn | Leu | Val | Leu | Ala | Asp | Cys | Gly | Ala | Gly | Phe | Phe | Asp | Pro |      |
|     | 530 |     |     |     |     | 535 |     |     |     |     | 540 |     |     |     |     |      |
| ctg | acc | cgc | ggc | gtg | ctg | tcc | acg | gtg | tcc | ggt | gtc | gtg | gtc | gtg | gca | 1680 |
| Leu | Thr | Arg | Gly | Val | Leu | Ser | Thr | Val | Ser | Gly | Val | Val | Val | Val | Ala |      |
| 545 |     |     |     |     | 550 |     |     |     |     | 555 |     |     |     |     | 560 |      |
| agt | gtc | tca | atc | gac | ggc | gca | caa | cag | gcg | tcg | gtc | gcg | ttg | gac | tgg | 1728 |

```
                Ser Val Ser Ile Asp Gly Ala Gln Gln Ala Ser Val Ala Leu Asp Trp
                            565                 570                 575 ttg cgc aac aac ggt tac caa gat ttg gcg agc cgc gca tgc gtg gtc    1776
Leu Arg Asn Asn Gly Tyr Gln Asp Leu Ala Ser Arg Ala Cys Val Val
            580                 585                 590 atc aat cac atc atg ccg gga gaa ccc aat gtc gca gtt aaa gac ctg    1824
Ile Asn His Ile Met Pro Gly Glu Pro Asn Val Ala Val Lys Asp Leu
            595                 600                 605 gtg cgg cat ttc gaa cag caa gtt caa ccc ggc cgg gtc gtg gtc atg    1872
Val Arg His Phe Glu Gln Gln Val Gln Pro Gly Arg Val Val Val Met
    610                 615                 620 ccg tgg gac agg cac att gcg gcc gga acc gag att tca ctc gac ttg    1920
Pro Trp Asp Arg His Ile Ala Ala Gly Thr Glu Ile Ser Leu Asp Leu
625                 630                 635                 640 ctc gac cct atc tac aag cgc aag gtc ctc gaa ttg gcc gca gcg cta    1968
Leu Asp Pro Ile Tyr Lys Arg Lys Val Leu Glu Leu Ala Ala Ala Leu
                    645                 650                 655 tcc gac gat ttc gag agg gct gga cgt cgt tga                         2001
Ser Asp Asp Phe Glu Arg Ala Gly Arg Arg
                660                 665

<210> SEQ ID NO 14
<211> LENGTH: 1536
<212> TYPE: DNA
<213> ORGANISM: Mycobacterium tuberculosis
<220> FEATURE:
<221> NAME/KEY: CDS
<222> LOCATION: (1)...(1533)

<400> SEQUENCE: 14 ttg agc gca cct gct gtt gct gct ggt cct acc gcc gcg ggg gca acc      48
Leu Ser Ala Pro Ala Val Ala Ala Gly Pro Thr Ala Ala Gly Ala Thr
1               5                   10                  15 gct gcg cgg cct gcc acc acc cgg gtg acg atc ctg acc ggc aga cgg     96
Ala Ala Arg Pro Ala Thr Thr Arg Val Thr Ile Leu Thr Gly Arg Arg
            20                  25                  30 atg acc gat ttg gta ctg cca gcg gcg gtg ccg atg gaa act tat att    144
Met Thr Asp Leu Val Leu Pro Ala Ala Val Pro Met Glu Thr Tyr Ile
        35                  40                  45 gac gac acc gtc gcg gtg ctt tcc gag gtg ttg gaa gac acg ccg gct    192
Asp Asp Thr Val Ala Val Leu Ser Glu Val Leu Glu Asp Thr Pro Ala
    50                  55                  60 gat gta ctc ggc ggc ttc gac ttt acc gcg caa ggc gtg tgg gcg ttc    240
Asp Val Leu Gly Gly Phe Asp Phe Thr Ala Gln Gly Val Trp Ala Phe
65                  70                  75                  80 gct cgt ccc gga tcg ccg ccg ctg aag ctc gac cag tca ctc gat gac    288
Ala Arg Pro Gly Ser Pro Pro Leu Lys Leu Asp Gln Ser Leu Asp Asp
                85                  90                  95 gcc ggg gtg gtc gac ggg tca ctg ctg act ctg gtg tca gtc agt cgc    336
Ala Gly Val Val Asp Gly Ser Leu Leu Thr Leu Val Ser Val Ser Arg
            100                 105                 110 acc gag cgc tac cga ccg ttg gtc gag gat gtc atc gac gcg atc gcc    384
Thr Glu Arg Tyr Arg Pro Leu Val Glu Asp Val Ile Asp Ala Ile Ala
        115                 120                 125 gtg ctt gac gag tca cct gag ttc gac cgc acg gca ttg aat cgc ttt    432
Val Leu Asp Glu Ser Pro Glu Phe Asp Arg Thr Ala Leu Asn Arg Phe
    130                 135                 140 gtg ggg gcg gcg atc ccg ctt ttg acc gcg ccc gtc atc ggg atg gcg    480
Val Gly Ala Ala Ile Pro Leu Leu Thr Ala Pro Val Ile Gly Met Ala
145                 150                 155                 160 atg cgg gcg tgg tgg gaa act ggg cgt agc ttg tgg tgg ccg ttg gcg    528
```

```
Met Arg Ala Trp Trp Glu Thr Gly Arg Ser Leu Trp Trp Pro Leu Ala
              165                 170                 175 att ggc atc ctg ggg atc gct gtg ctg gta ggc agc ttc gtc gcg aac      576
Ile Gly Ile Leu Gly Ile Ala Val Leu Val Gly Ser Phe Val Ala Asn
            180                 185                 190 agg ttc tac cag agc ggc cac ctg gcc gag tgc cta ctg gtc acg acg      624
Arg Phe Tyr Gln Ser Gly His Leu Ala Glu Cys Leu Leu Val Thr Thr
                195                 200                 205 tat ctg ctg atc gca acc gcc gca gcg ctg gcc gtg ccg ttg ccg cgc      672
Tyr Leu Leu Ile Ala Thr Ala Ala Ala Leu Ala Val Pro Leu Pro Arg
        210                 215                 220 ggg gtc aac tcg ttg ggg gcg cca caa gtt gcc ggc gcc gct acg gcc      720
Gly Val Asn Ser Leu Gly Ala Pro Gln Val Ala Gly Ala Ala Thr Ala
225                 230                 235                 240 gtg ctg ttt ttg acc ttg atg acg cgg ggc ggc cct cgg aag cgt cat      768
Val Leu Phe Leu Thr Leu Met Thr Arg Gly Gly Pro Arg Lys Arg His
                245                 250                 255 gag ttg gcg tcg ttt gcc gtg atc acc gct atc gcg gtc atc gcg gcc      816
Glu Leu Ala Ser Phe Ala Val Ile Thr Ala Ile Ala Val Ile Ala Ala
            260                 265                 270 gcc gct gcc ttc ggc tat gga tac cag gac tgg gtc ccc gcg ggg ggg      864
Ala Ala Ala Phe Gly Tyr Gly Tyr Gln Asp Trp Val Pro Ala Gly Gly
                275                 280                 285 atc gca ttc ggg ctg ttc att gtg acg aat gcg gcc aag ctg acc gtc      912
Ile Ala Phe Gly Leu Phe Ile Val Thr Asn Ala Ala Lys Leu Thr Val
        290                 295                 300 gcg gtc gcg cgg atc gcg ctg ccg ccg att ccg gta ccc ggc gaa acc      960
Ala Val Ala Arg Ile Ala Leu Pro Pro Ile Pro Val Pro Gly Glu Thr
305                 310                 315                 320 gtg gac aac gag gag ttg ctc gat ccc gtc gcg acc ccg gag gct acc     1008
Val Asp Asn Glu Glu Leu Leu Asp Pro Val Ala Thr Pro Glu Ala Thr
                325                 330                 335 agc gaa gaa acc ccg acc tgg cag gcc atc atc gcg tcg gtc ccc gcg     1056
Ser Glu Glu Thr Pro Thr Trp Gln Ala Ile Ile Ala Ser Val Pro Ala
            340                 345                 350 tcc gcg gtc cgg ctc acc gag cgc agc aaa ctg gcc aag caa ctt ctg     1104
Ser Ala Val Arg Leu Thr Glu Arg Ser Lys Leu Ala Lys Gln Leu Leu
                355                 360                 365 atc gga tac gtc acg tcg ggc acc ctg att ctg gct gcc ggt gcc atc     1152
Ile Gly Tyr Val Thr Ser Gly Thr Leu Ile Leu Ala Ala Gly Ala Ile
        370                 375                 380 gcg gtc gtg gtg cgc ggg cac ttc ttt gta cac agc ctg gtg gtc gcg     1200
Ala Val Val Val Arg Gly His Phe Phe Val His Ser Leu Val Val Ala
385                 390                 395                 400 ggt ttg atc acg acc gtc tgc gga ttt cgc tcg cgg ctt tac gcc gag     1248
Gly Leu Ile Thr Thr Val Cys Gly Phe Arg Ser Arg Leu Tyr Ala Glu
                405                 410                 415 cgc tgg tgt gcg tgg gcg ttg ctg gcg gcg acg gtc gcg att ccg acg     1296
Arg Trp Cys Ala Trp Ala Leu Leu Ala Ala Thr Val Ala Ile Pro Thr
            420                 425                 430 ggt ctg acg gcc aaa ctc atc atc tgg tac ccg cac tat gcc tgg ctg     1344
Gly Leu Thr Ala Lys Leu Ile Ile Trp Tyr Pro His Tyr Ala Trp Leu
                435                 440                 445 ttg ttg agc gtc tac ctc acg gta gcc ctg gtt gcg ctc gtg gtg gtc     1392
Leu Leu Ser Val Tyr Leu Thr Val Ala Leu Val Ala Leu Val Val Val
        450                 455                 460 ggg tcg atg gct cac gtc cgg cgc gtt tca ccg gtc gta aaa cga act     1440
Gly Ser Met Ala His Val Arg Arg Val Ser Pro Val Val Lys Arg Thr
465                 470                 475                 480
```

```
ctg gaa ttg atc gac ggc gcc atg atc gct gcc atc att ccc atg ctg    1488
Leu Glu Leu Ile Asp Gly Ala Met Ile Ala Ala Ile Ile Pro Met Leu
                485                 490                 495 ctg tgg atc acc ggg gtg tac gac acg gtc cgc aat atc cgg ttc        1533
Leu Trp Ile Thr Gly Val Tyr Asp Thr Val Arg Asn Ile Arg Phe
        500                 505                 510 tga                                                                 1536

<210> SEQ ID NO 15
<211> LENGTH: 843
<212> TYPE: DNA
<213> ORGANISM: Mycobacterium tuberculosis
<220> FEATURE:
<221> NAME/KEY: CDS
<222> LOCATION: (1)...(840)

<400> SEQUENCE: 15 atg gct gaa ccg ttg gcc gtc gat ccc acc ggc ttg agc gca gcg gcc    48
Met Ala Glu Pro Leu Ala Val Asp Pro Thr Gly Leu Ser Ala Ala Ala
1               5                   10                  15 gcg aaa ttg gcc ggc ctc gtt ttt ccg cag cct ccg gcg ccg atc gcg    96
Ala Lys Leu Ala Gly Leu Val Phe Pro Gln Pro Pro Ala Pro Ile Ala
            20                  25                  30 gtc agc gga acg gat tcg gtg gta gca gca atc aac gag acc atg cca    144
Val Ser Gly Thr Asp Ser Val Val Ala Ala Ile Asn Glu Thr Met Pro
        35                  40                  45 agc atc gaa tcg ctg gtc agt gac ggg ctg ccc ggc gtg aaa gcc gcc    192
Ser Ile Glu Ser Leu Val Ser Asp Gly Leu Pro Gly Val Lys Ala Ala
    50                  55                  60 ctg act cga aca gca tcc aac atg aac gcg gcg gcg gac gtc tat gcg    240
Leu Thr Arg Thr Ala Ser Asn Met Asn Ala Ala Ala Asp Val Tyr Ala
65                  70                  75                  80 aag acc gat cag tca ctg gga acc agt ttg agc cag tat gca ttc ggc    288
Lys Thr Asp Gln Ser Leu Gly Thr Ser Leu Ser Gln Tyr Ala Phe Gly
                85                  90                  95 tcg tcg ggc gaa ggc ctg gct ggc gtc gcc tcg gtc ggt ggt cag cca    336
Ser Ser Gly Glu Gly Leu Ala Gly Val Ala Ser Val Gly Gly Gln Pro
            100                 105                 110 agt cag gct acc cag ctg ctg agc aca ccc gtg tca cag gtc acg acc    384
Ser Gln Ala Thr Gln Leu Leu Ser Thr Pro Val Ser Gln Val Thr Thr
        115                 120                 125 cag ctc ggc gag acg gcc gct gag ctg gca ccc cgt gtt gtt gcg acg    432
Gln Leu Gly Glu Thr Ala Ala Glu Leu Ala Pro Arg Val Val Ala Thr
    130                 135                 140 gtg ccg caa ctc gtt cag ctg gct ccg cac gcc gtt cag atg tcg caa    480
Val Pro Gln Leu Val Gln Leu Ala Pro His Ala Val Gln Met Ser Gln
145                 150                 155                 160 aac gca tcc ccc atc gct cag acg atc agt caa acc gcc caa cag gcc    528
Asn Ala Ser Pro Ile Ala Gln Thr Ile Ser Gln Thr Ala Gln Gln Ala
                165                 170                 175 gcc cag agc gcg cag ggc ggc agc ggc cca atg ccc gca cag ctt gcc    576
Ala Gln Ser Ala Gln Gly Gly Ser Gly Pro Met Pro Ala Gln Leu Ala
            180                 185                 190 agc gct gaa aaa ccg gcc acc gag caa gcg gag ccg gtc cac gaa gtg    624
Ser Ala Glu Lys Pro Ala Thr Glu Gln Ala Glu Pro Val His Glu Val
        195                 200                 205 aca aac gac gat cag ggc gac cag ggc gac gtg cag ccg gcc gag gtc    672
Thr Asn Asp Asp Gln Gly Asp Gln Gly Asp Val Gln Pro Ala Glu Val
    210                 215                 220 gtt gcc gcg gca cgt gac gaa ggc gcc ggc gca tca ccg ggc cag cag    720
Val Ala Ala Ala Arg Asp Glu Gly Ala Gly Ala Ser Pro Gly Gln Gln
```

```
                225                 230                 235                 240
ccc ggc ggg ggc gtt ccc gcg caa gcc atg gat acc gga gcc ggt gcc     768
Pro Gly Gly Gly Val Pro Ala Gln Ala Met Asp Thr Gly Ala Gly Ala
                245                 250                 255 cgc cca gcg gcg agt ccg ctg gcg gcc ccc gtc gat ccg tcg act ccg     816
Arg Pro Ala Ala Ser Pro Leu Ala Ala Pro Val Asp Pro Ser Thr Pro
            260                 265                 270 gca ccc tca aca acc aca acg ttg tag                                 843
Ala Pro Ser Thr Thr Thr Thr Leu
        275                 280

<210> SEQ ID NO 16
<211> LENGTH: 2190
<212> TYPE: DNA
<213> ORGANISM: Mycobacterium tuberculosis
<220> FEATURE:
<221> NAME/KEY: CDS
<222> LOCATION: (1)...(2187)

<400> SEQUENCE: 16 atg agt att acc agg ccg acg ggc agc tat gcc aga cag atg ctg gat     48
Met Ser Ile Thr Arg Pro Thr Gly Ser Tyr Ala Arg Gln Met Leu Asp
1               5                  10                  15 ccg ggc ggc tgg gtg gaa gcc gat gaa gac act ttc tat gac cgg gcc     96
Pro Gly Gly Trp Val Glu Ala Asp Glu Asp Thr Phe Tyr Asp Arg Ala
                20                  25                  30 cag gaa tat agc cag gtt ttg caa agg gtc acc gat gta ttg gac acc    144
Gln Glu Tyr Ser Gln Val Leu Gln Arg Val Thr Asp Val Leu Asp Thr
            35                  40                  45 tgc cgc cag cag aaa ggc cac gtc ttc gaa ggc gga cta tgg tcc ggc    192
Cys Arg Gln Gln Lys Gly His Val Phe Glu Gly Gly Leu Trp Ser Gly
        50                  55                  60 ggc gcc gcc aat gct gcc aac ggc gcc ctg ggt gca aac atc aat caa    240
Gly Ala Ala Asn Ala Ala Asn Gly Ala Leu Gly Ala Asn Ile Asn Gln
65                  70                  75                  80 ttg atg acg ctg cag gat tat ctc gcc acg gtg att acc tgg cac agg    288
Leu Met Thr Leu Gln Asp Tyr Leu Ala Thr Val Ile Thr Trp His Arg
                85                  90                  95 cat att gcc ggg ttg att gag caa gct aaa tcc gat atc ggc aat aat    336
His Ile Ala Gly Leu Ile Glu Gln Ala Lys Ser Asp Ile Gly Asn Asn
                100                 105                 110 gtg gat ggc gct caa cgg gag atc gat atc ctg gag aat gac cct agc    384
Val Asp Gly Ala Gln Arg Glu Ile Asp Ile Leu Glu Asn Asp Pro Ser
            115                 120                 125 ctg gat gct gat gag cgc cat acc gcc atc aat tca ttg gtc acg gcg    432
Leu Asp Ala Asp Glu Arg His Thr Ala Ile Asn Ser Leu Val Thr Ala
        130                 135                 140 acg cat ggg gcc aat gtc agt ctg gtc gcc gag acc gct gag cgg gtg    480
Thr His Gly Ala Asn Val Ser Leu Val Ala Glu Thr Ala Glu Arg Val
145                 150                 155                 160 ctg gaa tcc aag aat tgg aaa cct ccg aag aac gca ctc gag gat ttg    528
Leu Glu Ser Lys Asn Trp Lys Pro Pro Lys Asn Ala Leu Glu Asp Leu
                165                 170                 175 ctt cag cag aag tcg ccg cca ccc cca gac gtg cct acc ctg gtc gtg    576
Leu Gln Gln Lys Ser Pro Pro Pro Pro Asp Val Pro Thr Leu Val Val
                180                 185                 190 cca tcc ccg ggc aca ccg ggc aca ccg gga acc ccg atc acc ccg gga    624
Pro Ser Pro Gly Thr Pro Gly Thr Pro Gly Thr Pro Ile Thr Pro Gly
            195                 200                 205 acc ccg atc acc ccg gga acc cca atc aca ccc atc ccg gga gcg ccg    672
Thr Pro Ile Thr Pro Gly Thr Pro Ile Thr Pro Ile Pro Gly Ala Pro
```

-continued

|     |     |     | 210 |     |     |     | 215 |     |     |     | 220 |     |     |      |
|-----|-----|-----|-----|-----|-----|-----|-----|-----|-----|-----|-----|-----|-----|------|
| gta | act | ccg | atc | aca | cca | acg | ccc | ggc | act | ccc | gtc | acg | ccg | gtg acc | 720 |
| Val | Thr | Pro | Ile | Thr | Pro | Thr | Pro | Gly | Thr | Pro | Val | Thr | Pro | Val Thr |
| 225 |     |     |     |     | 230 |     |     |     |     | 235 |     |     |     | 240 |

```
ccg ggc aag ccg gtc acc ccg gtg acc ccg gtc aaa ccg ggc aca cca       768
Pro Gly Lys Pro Val Thr Pro Val Thr Pro Val Lys Pro Gly Thr Pro
                245                 250                 255 ggc gag cca acc ccg atc acg ccg gtc acc ccc ccg gtc gcc ccg gcc       816
Gly Glu Pro Thr Pro Ile Thr Pro Val Thr Pro Pro Val Ala Pro Ala
            260                 265                 270 aca ccg gca acc ccg gcc acg ccc gtt acc cca gct ccc gct cca cac       864
Thr Pro Ala Thr Pro Ala Thr Pro Val Thr Pro Ala Pro Ala Pro His
        275                 280                 285 ccg cag ccg gct ccg gca ccg gcg cca tcg cct ggg ccc cag ccg gtt       912
Pro Gln Pro Ala Pro Ala Pro Ala Pro Ser Pro Gly Pro Gln Pro Val
    290                 295                 300 aca ccg gcc act ccc ggt ccg tct ggt cca gca aca ccg ggc acc cca       960
Thr Pro Ala Thr Pro Gly Pro Ser Gly Pro Ala Thr Pro Gly Thr Pro
305                 310                 315                 320 ggg ggc gag ccg gcg ccg cac gtc aaa ccc gcg gcg ttg gcg gag caa      1008
Gly Gly Glu Pro Ala Pro His Val Lys Pro Ala Ala Leu Ala Glu Gln
                325                 330                 335 cct ggt gtg ccg ggc cag cat gcg ggc ggg ggg acg cag tcg ggg cct      1056
Pro Gly Val Pro Gly Gln His Ala Gly Gly Gly Thr Gln Ser Gly Pro
            340                 345                 350 gcc cat gcg gac gaa tcc gcc gcg tcg gtg acg ccg gct gcg gcg tcc      1104
Ala His Ala Asp Glu Ser Ala Ala Ser Val Thr Pro Ala Ala Ala Ser
        355                 360                 365 ggt gtc ccg ggc gca cgg gcg gcg gcc gcg ccg agc ggt acc gcc           1152
Gly Val Pro Gly Ala Arg Ala Ala Ala Ala Pro Ser Gly Thr Ala
    370                 375                 380 gtg gga gcg ggc gcg cgt tcg agc gtg ggt acg gcc gcg gcc tcg ggc      1200
Val Gly Ala Gly Ala Arg Ser Ser Val Gly Thr Ala Ala Ala Ser Gly
385                 390                 395                 400 gcg ggg tcg cat gct gcc act ggg cgg gcg ccg gtg gct acc tcg gac      1248
Ala Gly Ser His Ala Ala Thr Gly Arg Ala Pro Val Ala Thr Ser Asp
                405                 410                 415 aag gcg gcg gca ccg agc acg cgg gcg gcc tcg gcg cgg acg gca cct      1296
Lys Ala Ala Ala Pro Ser Thr Arg Ala Ala Ser Ala Arg Thr Ala Pro
            420                 425                 430 cct gcc cgc ccg ccg tcg acc gat cac atc gac aaa ccc gat cgc agc      1344
Pro Ala Arg Pro Pro Ser Thr Asp His Ile Asp Lys Pro Asp Arg Ser
        435                 440                 445 gag tct gca gat gac ggt acg ccg gtg tcg atg atc ccg gtg tcg gcg      1392
Glu Ser Ala Asp Asp Gly Thr Pro Val Ser Met Ile Pro Val Ser Ala
    450                 455                 460 gct cgg gcg gca cgc gac gcc gcc act gca gct gcc agc gcc cgc cag      1440
Ala Arg Ala Ala Arg Asp Ala Ala Thr Ala Ala Ala Ser Ala Arg Gln
465                 470                 475                 480 cgt ggc cgc ggt gat gcg ctg cgg ttg gcg cga cgc atc gcg gcg gcg      1488
Arg Gly Arg Gly Asp Ala Leu Arg Leu Ala Arg Arg Ile Ala Ala Ala
                485                 490                 495 ctc aac gcg tcc gac aac aac gcg ggc gac tac ggg ttc ttc tgg atc      1536
Leu Asn Ala Ser Asp Asn Asn Ala Gly Asp Tyr Gly Phe Phe Trp Ile
            500                 505                 510 acc gcg gtg acc acc gac ggt tcc atc gtc gtg gcc aac agc tat ggg      1584
Thr Ala Val Thr Thr Asp Gly Ser Ile Val Val Ala Asn Ser Tyr Gly
        515                 520                 525 ctg gcc tac ata ccc gac ggg atg gaa ttg ccg aat aag gtg tac ttg      1632
```

```
                                                                         -continued Leu Ala Tyr Ile Pro Asp Gly Met Glu Leu Pro Asn Lys Val Tyr Leu
    530                 535                 540 gcc agc gcg gat cac gca atc ccg gtt gac gaa att gca cgc tgt gcc    1680
Ala Ser Ala Asp His Ala Ile Pro Val Asp Glu Ile Ala Arg Cys Ala
545                 550                 555                 560 acc tac ccg gtt ttg gcc gtg caa gcc tgg gcg gct ttc cac gac atg    1728
Thr Tyr Pro Val Leu Ala Val Gln Ala Trp Ala Ala Phe His Asp Met
                565                 570                 575 acg ctg cgg gcg gtg atc ggt acc gcg gag cag ttg gcc agt tcg gat    1776
Thr Leu Arg Ala Val Ile Gly Thr Ala Glu Gln Leu Ala Ser Ser Asp
                580                 585                 590 ccc ggt gtg gcc aag att gtg ctg gag cca gat gac att ccg gag agc    1824
Pro Gly Val Ala Lys Ile Val Leu Glu Pro Asp Asp Ile Pro Glu Ser
            595                 600                 605 ggc aaa atg acg ggc cgg tcg cgg ctg gag gtc gtc gac ccc tcg gcg    1872
Gly Lys Met Thr Gly Arg Ser Arg Leu Glu Val Val Asp Pro Ser Ala
    610                 615                 620 gcg gct cag ctg gcc gac act acc gat cag cgt ttg ctc gac ttg ttg    1920
Ala Ala Gln Leu Ala Asp Thr Thr Asp Gln Arg Leu Leu Asp Leu Leu
625                 630                 635                 640 ccg ccg gcg ccg gtg gat gtc aat cca ccg ggc gat gag cgg cac atg    1968
Pro Pro Ala Pro Val Asp Val Asn Pro Pro Gly Asp Glu Arg His Met
                645                 650                 655 ctg tgg ttc gag ctg atg aag ccc atg acc agc acc gct acc ggc cgc    2016
Leu Trp Phe Glu Leu Met Lys Pro Met Thr Ser Thr Ala Thr Gly Arg
                660                 665                 670 gag gcc gct cat ctg cgg gcg ttc cgg gcc tac gct gcc cac tca cag    2064
Glu Ala Ala His Leu Arg Ala Phe Arg Ala Tyr Ala Ala His Ser Gln
            675                 680                 685 gag att gcc ctg cac caa gcg cac act gcg act gac gcg gcc gtc cag    2112
Glu Ile Ala Leu His Gln Ala His Thr Ala Thr Asp Ala Ala Val Gln
    690                 695                 700 cgt gtg gcc gtc gcg gac tgg ctg tac tgg caa tac gtc acc ggg ttg    2160
Arg Val Ala Val Ala Asp Trp Leu Tyr Trp Gln Tyr Val Thr Gly Leu
705                 710                 715                 720 ctc gac cgg gcc ctg gcc gcc gca tgc tga                            2190
Leu Asp Arg Ala Leu Ala Ala Ala Cys
                725
```